(12) United States Patent
Higuma et al.

(10) Patent No.: US 6,464,708 B1
(45) Date of Patent: Oct. 15, 2002

(54) CONTINUOUS LIGATION KIT

(75) Inventors: Masato Higuma; Haruhiko Masuda, both of Akita (JP)

(73) Assignee: Sumitomo Bakelite Co., Ltd., Tokyo (JP)

( * ) Notice: Subject to any disclaimer, the term of this patent is extended or adjusted under 35 U.S.C. 154(b) by 0 days.

(21) Appl. No.: 09/529,697

(22) PCT Filed: Aug. 20, 1999

(86) PCT No.: PCT/JP99/04475

§ 371 (c)(1),
(2), (4) Date: Jun. 19, 2000

(87) PCT Pub. No.: WO00/10468

PCT Pub. Date: Mar. 2, 2000

(30) Foreign Application Priority Data

| Aug. 20, 1998 | (JP) | 10-233735 |
| Dec. 21, 1998 | (JP) | 10-361785 |
| Apr. 23, 1999 | (JP) | 11-117209 |

(51) Int. Cl.[7] ............................................ A61B 17/04
(52) U.S. Cl. ............................ 606/140; 606/139
(58) Field of Search .................. 606/139, 140, 606/141

(56) References Cited

U.S. PATENT DOCUMENTS

| 5,398,844 A | 3/1995 | Zaslavsky et al. | 221/208 |
| 5,462,559 A | 10/1995 | Ahmed | 606/140 |
| 5,507,797 A | 4/1996 | Suzuki et al. | 606/140 |
| 6,099,535 A | * 8/2000 | Lamport et al. | 606/140 |

FOREIGN PATENT DOCUMENTS

| JP | 7-59786 | 3/1995 | A61B/17/12 |
| JP | 8-10217 | 1/1996 | A61B/1/00 |
| JP | 8-502198 | 3/1996 | A61B/17/12 |
| JP | 2561223 | 9/1996 | A61B/17/12 |
| JP | 9-500811 | 1/1997 | A61B/17/00 |
| JP | 2657427 | 6/1997 | A61B/17/12 |
| JP | 10-14925 | 1/1998 | A61B/17/00 |
| JP | 10-179596 | 7/1998 | A61B/17/00 |
| JP | 10-201765 | 8/1998 | A61B/17/00 |

* cited by examiner

*Primary Examiner*—David O. Reip
*Assistant Examiner*—Julian W. Woo
(74) *Attorney, Agent, or Firm*—Caesar, Rivise, Bernstein, Cohen & Pokotilow, Ltd.

(57) ABSTRACT

A fluid circuit connects a pressure applying portion (17, 20) and a distal device (1) to charge fluid into the distal device (1). The fluid circuit includes a controller (10, 11) to control the movement of ligating rings (13). The controller (10, 11) senses a pressure drop in the distal device (1) when one or a plural number of the ligating rings (13) are separated from the distal device (1). The movement of the ligating rings (13) is stopped in accordance with the pressure drop so that at least two or more of the ligating rings can be separated at a time. Accordingly, ligation of esophageal varices and internal hemorrhoids can be performed successively.

20 Claims, 15 Drawing Sheets

CONTINUOUS LIGATION KIT

BACKGROUND OF THE INVENTION

The present invention relates to a ligation instrument, which is used during ligation of stomach or esophageal varices and internal hemorrhoids, that enables safe and ensure treatment through simple manipulation.

BACKGROUND ART

Endoscopic variceal ligation (hereafter referred to as EVL) is performed to treat varices of the stomach and the esophagus caused by hepatocirrhosis or other reasons. EVL is a manipulation performed as follows. Referring to FIG. 36, a varix (39) is drawn into a cylinder (38) connected to a front portion of an endoscope (2) so that the varix becomes fungus-like. A ligating ring (13), which is fitted beforehand about the front portion of the cylinder (38), is removed by manipulating a wire inserted through a forceps passage (43) (refer to FIG. 35) and hooked to the basal section of the fungus-like varix (39). The elasticity of the rubber ligating ring (13) mechanically ligates the varix (39).

U.S. Pat. No. 4,735,194 describes a conventional ligation instrument, which is shown in FIG. 35, used when performing EVL. The ligation instrument has a cylinder (38) fixed to a coupling portion (40) defined at the front end of an endoscope (2). A slide tube (4), to which a ligating ring (13) is fitted, is fitted in the cylinder (38) so that the slide tube (4) can slide within the cylinder (38). The slide tube (4) is fixed to a trip wire (41), which extends through a forceps passage (43) of the endoscope (2). In this structure, when the trip wire (41) is pulled, the slide tube (4) is retracted, and the front end of the cylinder. (38) is separated from the ligating ring (13).

FIG. 34 shows a different ligation instrument, which is used to perform EVL and is driven by air. A slide tube (4), the rear end of which is surrounded by a seal ring (7), is provided between an inner tube (5), to which a ligating ring (13) is fitted, and an outer tube (3),. These parts define a hermetic space, the rear end of which is provided with a small hole. The small hole is connected to a fluid tube (9) (refer to Japanese Unexamined Patent Publication No. 7-059786, U.S. Pat. No. 5,507,797). In this structure, a syringe (44) forces air through a connector (45) and a fluid tube (9) to extend the slide tube (4) and separate the ligating ring (13).

In each of the ligation instruments, only one ligating ring (13) is connected to the inner tube. Thus, to perform the ligation treatment on a plurality of varices (39), the endoscope must be taken out of the body cavity every time to attach a ligating ring (13) and then returned into the body cavity. Accordingly, to perform ligations on a plurality of varices (39), the endoscope (2) must be moved in and out of the body cavity a number of times in correspondence with the number of varices (39). This lengthens the treatment time and subjects the patient to a large amount of pain.

To solve this problem, many ligation instruments that perform ligations successively with the endoscope (2) kept in the body cavity have been proposed (e.g., Japanese Unexamined Patent Publication No. 8-10217, Japanese Unexamined Patent Publication No. 8-502198, Japanese Unexamined Patent Publication No. 9-500811, Japanese Patent No. 2561223, Japanese Patent No. 2657427, U.S. Pat. No. 5,398,844, U.S. Pat. No. 5,462,559). However, these instruments use wires similar to that of the ligation instrument: shown in FIG. 35 and still do not provide solutions to various problems. These problems are:

(i) The single forceps passage (43) in the endoscope (2) cannot be used;

(ii) When the endoscope (2) is strongly reversed, sufficient force may not be transmitted to the front end of the trip wire (41) even if the trip wire (41) is pulled strongly. This may hinder the separation of the ligating ring (13);

(iii) It is difficult to perceive the separation of a ligating ring (13). Thus, a ligating ring (13) may not be separated or a plurality of the ligating rings s(13) may accidentally be separated at the same time; and (iv) The attached ligating rings (13) block the operator's view.

The conventional ligation instrument of FIG. 34 may solve problems (i) and (ii) but cannot not solve problems (iii) and (iv). Further, it cannot perform ligation successively with the endoscope (2) left in the body cavity.

The present invention provides a solution to the above problems. It is an object of the present invention to provide a successive ligation instrument that performs ligation successively in a safe and ensure manner with the endoscope remaining in the body cavity.

SUMMARY OF THE INVENTION

In a successive ligation instrument for ligating a lesion, a fluid is charged into a distal device attached to an endoscope to apply pressure to push forward and separate a ligating ring attached to the distal device. The present invention is characterized by a pressure applying means for charging the fluid into the distal device, and a controller connected to a fluid circuit to control the movement of the ligating ring to sense a pressure drop that occurs in the distal device when one or a plural number of the ligating rings are separated. The movement of the ligating rings is stopped in, accordance with the pressure drop so that at least two or more of the ligating rings are separated.

DETAILED DESCRIPTION OF THE PREFERRED EMBODIMENTS

Figure 1:
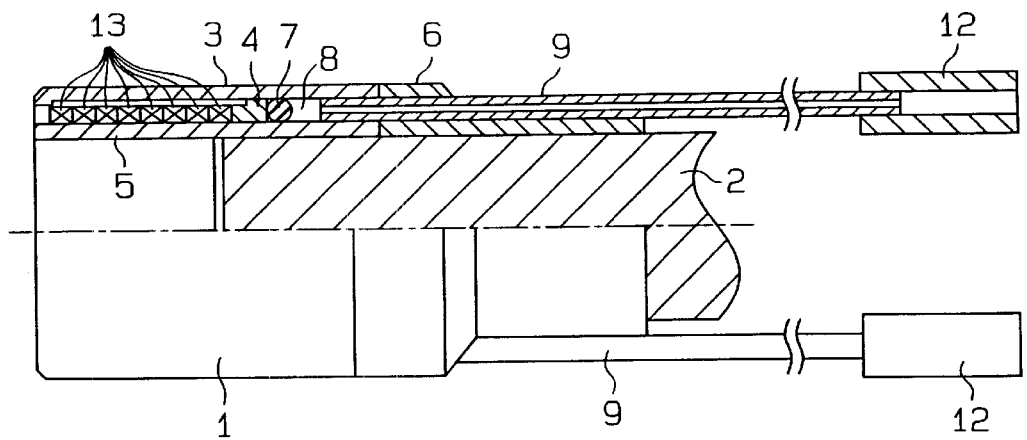
FIG. 1 is a specific cross-sectional view showing a distal device of a successive ligation kit according to an embodiment of the present invention that is attached to an endoscope.

An embodiment according to the present invention will now be described with reference to the drawings. FIG. 1 is a cross-sectional view showing a distal device (1) of a successive ligation apparatus according to an embodiment of the present invention that is attached to an endoscope (2). In the distal device (1), as shown in FIG. 1, a slide tube (4), which has a flange extending about the periphery of its rear end, is accommodated in an outer tube (3), which has a flange extending about its front end. Further, an inner tube (5) is fitted in the interior of the distal device.

The slide tube (4) is movable along the center axis of the distal device (1). The movement of the slide tube at the front end of the device is determined by contact between the flange of the outer tube (3) and the flange of the slide tube (4). A coupling tube (6) is arranged at the rear end of the inner tube (5) to fix the distal device (1) to the endoscope. A seal ring (7) attached to the rear end of the slide tube (4), the outer tube (3), and the inner tube (5), to define a hermetic space (8) at the rear of the seal ring (7). At least one fluid tube (9) is connected to the rear end of the hermetic space (8) for the passage of fluid. FIG. 1 shows two fluid tubes. A connector (12) is arranged at the rear end of each fluid tube (9) to connect each tube (9) to a controller (10) or a driver (11).

A plurality of ligating rings (13) are arranged in series along the center axis of the distal device (1) at the periphery of the front end of the inner tube (5). The number of the attached ligating rings (13) is not limited and may be determined in accordance with the application. For example, when treating esophageal varices, it is preferred that eight ligating rings (13) be used since eight ligations are often performed during a single treatment.

Embodiment of Manual Pressure Application

An example for performing pressure application of the ligating rings (13) manually will now be described. In the successive ligation apparatus according to the present invention, the controller (10) includes a pressure detecting portion, or pressure fluctuation measuring portion (14), a waveform processing portion (15), a control portion (16), a manual pressure applying portion (17), and a pressure releasing portion (18). The connection of the pressure fluctuation measuring portion (14), the manual pressure applying portion (17), and the pressure releasing portion (18) is not limited in any manner and may be connected or arranged as shown in FIG. 2 to FIG. 5.

Figure 2:
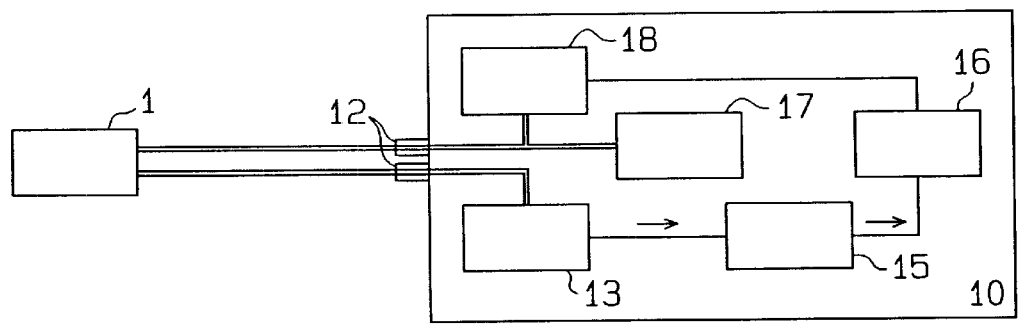
FIGS. 2 to 17 are diagrams showing the entire structure of ligation instruments in each of the embodiments according to the present invention.

In the example of the controller (10) shown in FIG. 2, two of the fluid tubes (9) connected to the hermetic space (8) are attached to the distal device (1). One end of the first fluid tube (9) is connected to the distal device (1), while the other end is connected to the pressure fluctuation measuring portion (14). One end of the second fluid tube (9) is connected to the distal device (1), while the other end is connected to the manual pressure applying portion (17) and the pressure releasing portion (18).

Figure 3:
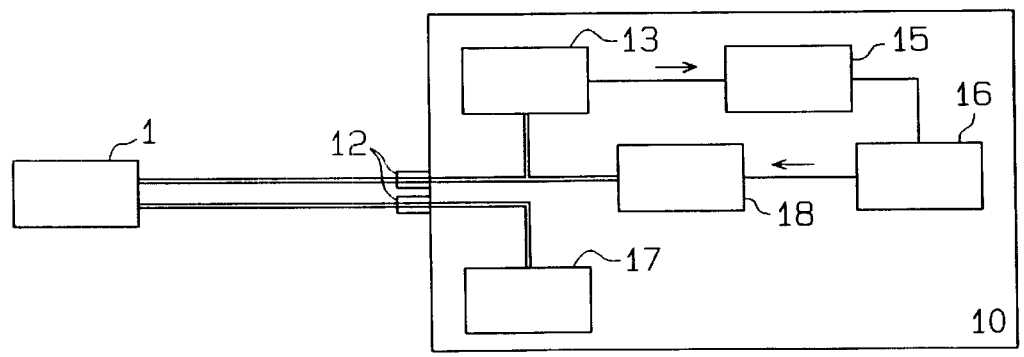

In the example of the controller (10) shown in FIG. 3, two of the fluid tubes (9) connected to the hermetic space (8) are attached to the distal device (1). One end of the first fluid tube (9) is connected to the distal device (1), while the other end is connected to the pressure fluctuation measuring portion (14) and the pressure releasing portion (18). One end of the second fluid tube (9) is connected to the distal device (1), while the other end is connected to the manual pressure applying portion (17).

Figure 4:
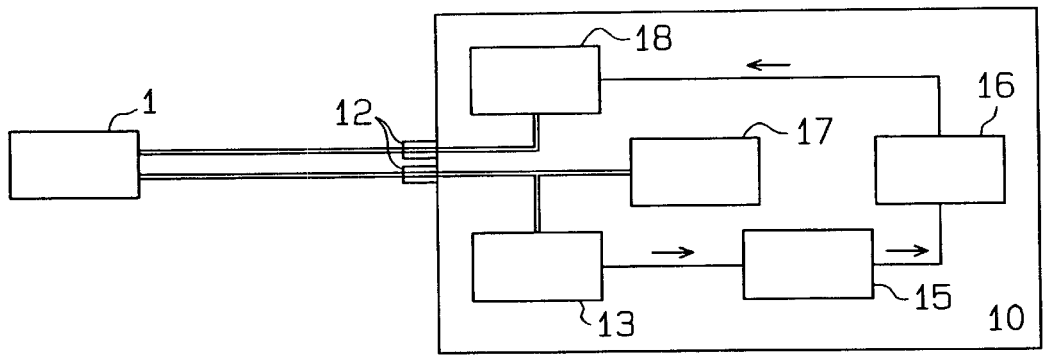

In the example of the controller (10) shown in FIG. 4, two of the fluid tubes (9) connected to the hermetic space (8) are attached to the distal device (1). One end of the first fluid tube (9) is connected to the distal device (1), while the other end is connected to the pressure releasing portion (18). One end of the second fluid tube (9) is connected to the distal device (1), while the other end is connected to the pressure fluctuation measuring portion (14) and the manual pressure applying portion (17).

Figure 5:
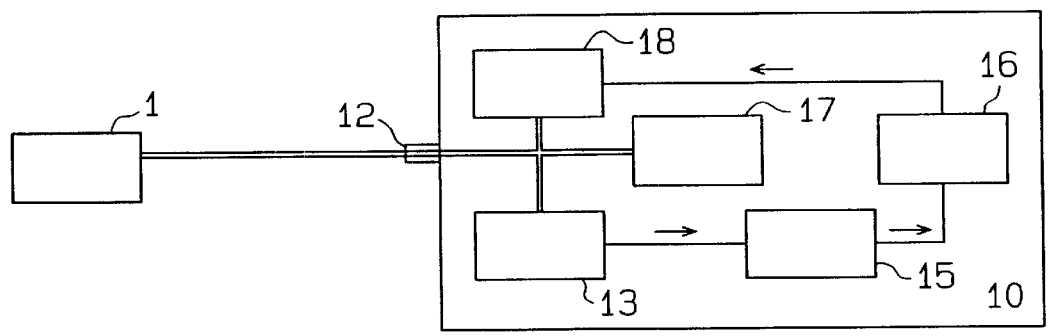

In the example of the controller (10) shown in FIG. 5, one of the fluid tubes (9) connected to the hermetic space (8) is attached to the distal device (1). One end of the fluid tube (9) is connected to the distal device (1), while the other end is connected to the pressure fluctuation measuring portion (14), the manual pressure applying portion (17), and the pressure releasing portion (18).

In each of the above controllers, the control portion (16) is electrically connected to the waveform processing portion (15) and the pressure releasing portion (18). The waveform processing portion (15) is electrically connected to the pressure fluctuation measuring portion (14). The operation of the successive ligation apparatus, which includes the controller (10) and the distal device (1) will now be discussed. The number of ligating rings (13) that are to be separated are first input to and stored in the control portion (16). The surgeon then manually manipulates the manual pressure applying portion (17) to produce sufficient positive pressure for driving the slide tube (4) and conveys the positive pressure to the hermetic space (8) in the distal device (1) through the fluid tube (9), which is connected to a fluid circuit.

In this state, since the pressure releasing portion, (18) and the pressure fluctuation measuring portion (14), which are controlled by the control portion (16), are closed from the exterior, the interior pressure of the hermetic space (8) in the distal device (1) increases. As a result, the slide tube (4) is moved toward the front by the seal ring (7). Simultaneously, the plurality of the ligating rings (13) are pushed together by the slide tube (4) and start to move toward the front of the distal device (1). At this time, changes in the interior pressure of the fluid circuit, which is connected to the hermetic space (8), are constantly measured by the pressure fluctuation measuring portion (14). When the frontmost ligating ring (13) passes by the frontmost portion of the inner tube (5), the first ligating ring (13) is separated from the distal device (1).

The load of the slide tube (4) decreases momentarily and causes the interior pressure of the fluid circuit to drop within a short period of time. Further continuation of the pressure application separates the second and subsequent ligating rings (13). A pressure drop occurs during each separation. The pressure fluctuation waveform resulting from the pressure drop is converted to an electrical waveform by the pressure fluctuation measuring portion (14) input to the waveform processing portion (15). The waveform processing portion (15) performs waveform processing of the input electrical waveform and outputs to the control portion (16) a signal indicating a pressure drop at substantially the same time as the pressure drop in accordance with the number of separations of the ligating rings (13). The control portion (16) counts the number of separations and outputs a control signal to the pressure releasing portion (18) when the number of separations reaches a prestored value.

Consequently, the pressure releasing portion (18) enters an opened state, releases the interior pressure of the fluid circuit to the exterior, and thus decreases the interior pressure in a sudden manner. This stops the movement of the slide tube (4), stops the movement of the ligating rings (13) subsequent to the last ring of the set number of the separated rings, and stops the separation. To perform ligation again at another lesion, the above operation is repeated to separate a certain number of the ligating rings (13). That is, after closing the pressure releasing portion (18), the number of ligating rings (13) to be separated is set, and that number of ligating rings (13) are separated by applying pressure with the manual pressure applying portion (17).

The operation speed required for the controller (10) is limited by the time necessary from when the final ligating ring (13) of the set number of separated ligating rings (13) for a single treatment is separated until the first ligating ring (13) of the set number of separated ligating rings (13) of the next treatment is separated. In this embodiment, the necessary time is 50 ms to 200 ms. Thus, it is required that the operation time for the procedures occuring from when the final ligating ring (13) of the first treatment is separated to when the first ligating ring (13) of the next treatment stops be 50 ms or less, and it is further preferred that the time be 30 ms or less.

It is required that the manual pressure applying portion (17) have the ability to produce enough pressure for moving two or more of the ligating rings (13), which are connected to the distal device (1), toward the front. In this embodiment, although it depends on the slide resistance of the inner tube (4) during movement of the ligating rings (13), a pressure of 5 kgf/cm$^2$ to 30 kgf/cm$^2$ is required when eight of the ligating rings (13) are connected. In this embodiment, the manual pressure applying portion (17) is formed by a small diameter syringe or an inflation syringe. When pressure is applied by the syringe, with fluid charged into the syringe, a piston is moved manually to compress the fluid and produce positive pressure. It should be noted that the volume of the syringe must be sufficient for separating the set number of ligating rings (13) and that the cylinder diameter must correspond to the user's strength, since a larger cylinder diameter requires more pressurizing force.

Although the pressure releasing portion (18) is not limited to any particular structure, the present embodiment uses an electromagnetic valve. The electromagnetic valve is required to be capable of sufficiently resisting the interior pressure produced in the fluid circuit and to have a response time that satisfies the requirements for the operating time of the driver (11). It is preferred that the electromagnetic valve of this embodiment have an operational pressure range of 10 kgf/cm$^2$ or more, and more preferably, 20 kgf/cm$^2$ or more, and that the. response time be 5 ms or less, and more preferably, 2 ms or less. Further, it is required that the employed fluid resist corrosion and that the fluid circuit be formed from a material that resists corrosion.

If there is a possibility that the interior of the electromagnetic valve may be corroded by the employed fluid, a pinch valve having a DC solenoid or the like capable of connecting the fluid tube (9) from the exterior may be used as the pressure releasing portion (18). In this case, the same operational pressure range and response time as described above are required.

When using a liquid as the fluid, if the electromagnetic valve is used when charging the fluid prior to usage, the lands and pits of the interior passage may result in residual air, depending on the selected magnetic valve. The residual air may interfere with the required direct pressure fluctuation measurement. However, since the fluid passage of the pinch valve is the fluid tube (9) itself, there is no residual air.

The waveform processing portion (15) is required to have a response time that satisfies the operation time of the controller (10). In this embodiment, the waveform processing portion (15) is formed by a differentiating circuit and a comparator circuit. The voltage input by the pressure fluctuation measuring portion (14) is first converted (amplified) to a voltage that is proportional to the fluctuation by the differentiating circuit, which is formed by an operational amplifier or the like, and then compared with a predetermined voltage threshold value by the comparator circuit, which is formed by an operational amplifier or the like, to generate a signal output when the threshold value is exceeded or a signal output when the threshold value is not exceeded.

In the above structure, pressure drops occur in the fluid circuit when the ligating rings (13) are separated. When the fluctuation amount of the pressure exceeds the predetermined threshold value, it is determined that a ligating ring (13) has been separated, and a signal to the control portion (16) is instantaneously sent.

A microcomputer may be used as the waveform processing portion (15). In this case, the voltage input by the pressure fluctuation measuring portion (14) is AD converted by an AD converter and then input to the microcomputer. The input voltages are input continuously in constant, short time intervals, and the difference between two consecutive input voltages (substraction value) is computed. Acknowledgement of an increase in the substraction value resulting from a drop in the interior pressure of the fluid circuit when a ligating ring (13) is separated causes the separation of the ligating ring (13) to be recognized. Further, when using the microcomputer, the conditions for determining that a ligating ring (13) has been separated from the substraction value may be programmed to be limited to the substraction value obtained during an interior pressure drop of the fluid circuit. This distinguishes electrical noise from interior pressure drops that occur when the ligating rings (13) slide in the distal device (1) and results in an instantaneous signal to the control portion (16) without erroneous actions.

The control portion (16) is also required to have a response time that satisfies the operation time of the driver (11). In this embodiment, a microcomputer or a sequencer capable of high speed processing is employed. That is, in this embodiment, the number of separated ligating rings (13) is stored through digital input or the like based on a prestored operation program. A signal indicating separation of the ligating rings (13) is input by the waveform processing portion (15). At least a function for outputting a signal to the pressure releasing portion (18) to open the pressure releasing portion (18) when the number of separated ligating rings (13) reaches a predetermined value is provided. The control portion (16) may be a circuit formed by only logic circuits, transistors, or the like, and do not have to employ a microcomputer or a sequencer. The separated number of ligating rings (13) may be counted by an internal counter or a counter attached externally, if a sequencer is used, or through internal subtractions or the like executed by a program, if a microcomputer is used.

Further Embodiment of Manual Pressure Application

As another example of applying pressure manually, the controller (10) may be formed as shown in FIGS. 6 to 9. In this successive ligation apparatus the controller (10) includes a pressure fluctuation measuring portion (14), a waveform processing portion (15), a control portion (16), a manual pressure applying portion (17), a pressure releasing portion (18), and a pressure blocking portion (19). The connection of the pressure fluctuation measuring portion the (14), the pressure releasing portion (18), the pressure blocking portion (19), and the manual pressure applying portion (17) are not limited in any manner and may be connected or arranged as shown in FIG. 6 to FIG. 9.

Figure 6:
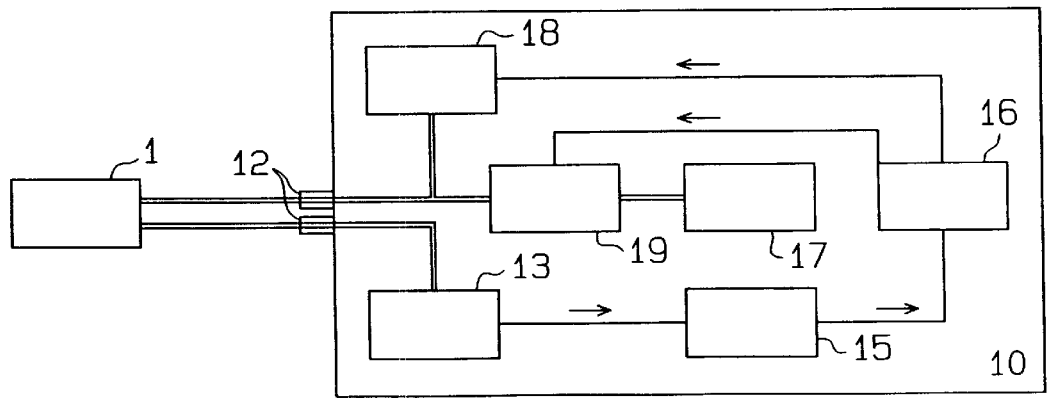

In the example of the controller (10) shown in FIG. 6, two of the fluid tubes (9) connected to the hermetic space (8) are attached to the distal device (1). One end of the first fluid tube (9) is connected to the distal device (1), while the other end is connected to the pressure fluctuation measuring portion (14). One end of the second fluid tube (9) is connected to the distal device (1), while the other end is connected to the manual pressure applying portion (17) and the pressure releasing portion (18). The pressure blocking portion (19) is connected between the pressure releasing portion (18) and the manual pressure applying portion (17).

Figure 7:
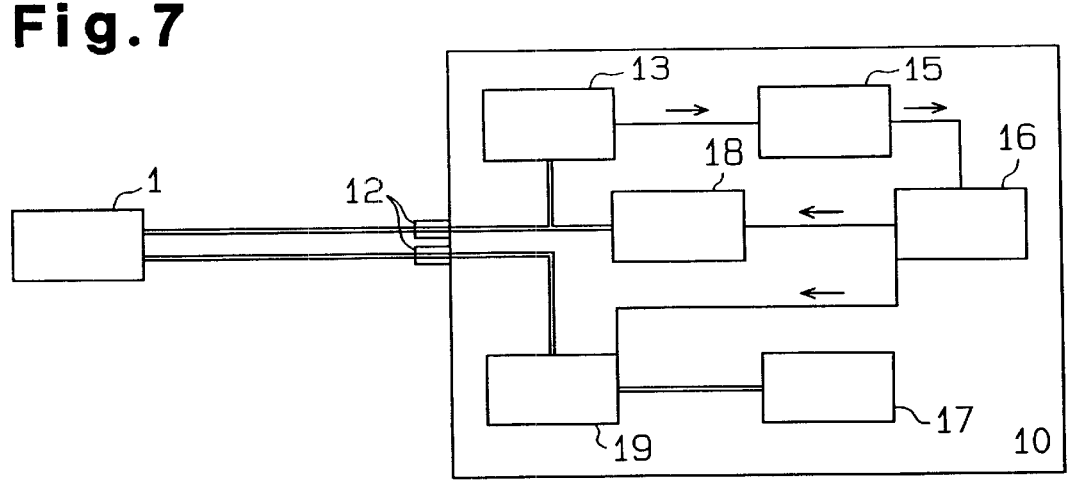

In the example of the controller (10) shown in FIG. 7, two of the fluid tubes (9) connected to the hermetic space (8) are attached to the distal device (1). One end of the first fluid tube (9) is connected to the distal device (1), while the other end is connected to the pressure fluctuation measuring portion (14) and the pressure releasing portion (18). One end of the second fluid tube (9) is connected to the distal device (1), while the other end is connected to the manual pressure applying portion (17). The pressure blocking portion (19) is connected between the manual pressure applying portion (17) and the distal device (1).

Figure 8:
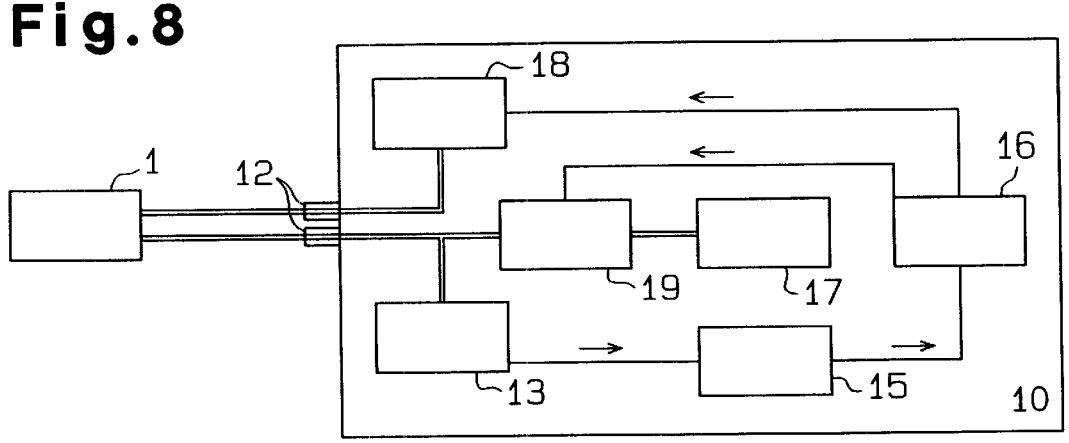

In the example of the controller (10) shown in FIG. 8, two of the fluid tubes (9) connected to the hermetic space (8) are attached to the distal device (1). One end of the first fluid tube (9) is connected to the distal device (1), while the other end is connected to the pressure releasing portion (18). One end of the second fluid tube (9) is connected to the distal device (1), while the other end is connected to the pressure fluctuation measuring portion (14) and the manual pressure applying portion (17). The pressure blocking portion (19) is connected between the manual pressure applying portion (17) and the pressure fluctuation measuring portion (14).

Figure 9:
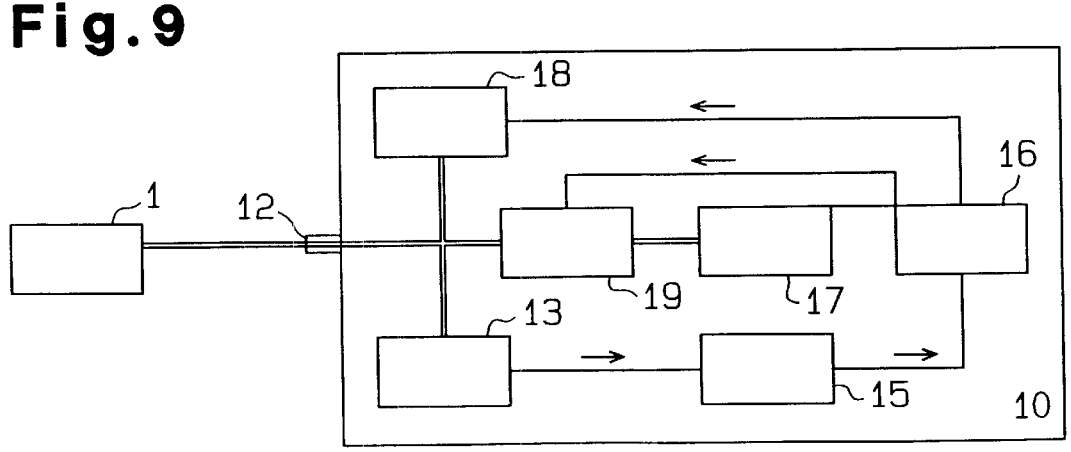

Further, in the example of the controller (10) shown in FIG. 9, one of the fluid tubes (9) connected to the hermetic space (8) is attached to the distal device (1). One end of the fluid tube (9) is connected to the distal device (1), while the other end is connected to the pressure fluctuation measuring portion (14), the manual pressure applying portion (17), and the pressure releasing portion (18). The pressure blocking portion. (19) is connected between the manual pressure applying portion (17) and the pressure fluctuation measuring portion (14) or the pressure releasing portion (18).

The control portion (16) is electrically connected to the waveform processing portion (15), the pressure releasing portion (18), and the pressure blocking portion (19). The waveform processing portion (15) is electrically connected to the pressure fluctuation measuring portion (14).

The operation of the successive ligation apparatus, which includes the controller (10) and the distal device (1) will now be discussed. The number of ligating rings (13) that are to be separated are first input to and stored in the control portion (16). The surgeon then manually manipulates the manual pressure applying portion (17) to produce sufficient positive pressure for driving the slide tube (4) and conveys the positive pressure to the hermetic space (8) in the distal device (1) through the fluid tube (9), which is connected to a fluid circuit.

In this state, since the pressure releasing portion (18) and the pressure fluctuation measuring portion (14), which are controlled by the control portion (16), are closed from the exterior, and since the pressure blocking portion (19) is in a closed state, the interior pressure of the hermetic space (8) in the distal device (1) increases. As a result, the slide tube (4) is moved toward the front of the distal device by the seal ring (7). Simultaneously, the plurality of ligating rings (13) are pushed together by the slide tube (4) and start to move toward the front of the distal device (1). At this time, changes in the interior pressure of the fluid circuit, which is connected to the hermetic space (8), are constantly measured by the pressure fluctuation measuring portion (14). When the frontmost ligating ring (13) passes by the frontmost portion of the inner tube (5), the first ligating ring (13) is separated from the distal device (1).

The load of the slide tube (4) that pushes the ligating rings (13) decreases momentarily and causes the interior pressure of the fluid circuit to drop within a short period of time. Further continuation of the pressure application separates the second and subsequent ligating rings (13). A pressure drop occurs during each separation. The pressure fluctuation waveform resulting from the pressure drop is converted to an electrical waveform by the pressure fluctuation measuring portion (14) and input to the waveform processing portion (15). The waveform processing portion (15) performs waveform processing of the input electrical waveform and outputs to the control portion (16) a signal indicating a pressure drop at substantially the same time as the pressure drop in accordance with the number of separation; of the ligating rings (13). The control portion (16) counts the number of separations and outputs a control signal to the pressure releasing portion (18) and the pressure blocking portion (19) when the number of separations reaches a prestored value.

Consequently, the pressure releasing portion (18) enters an opened state and releases the interior pressure of the fluid circuit to the exterior. The pressure blocking portion (19) enters a closed state and blocks the pressure applied by the fluid from the manual pressure applying portion (17). This decreases the interior pressure in the circuit in a sudden manner and stops the movement of the slide tube (4), stops the movement of the ligating rings (13) subsequent to the last ring of the set number of the separated rings, and stops separation. To perform ligation again at another lesion, the above operation is repeated to separate a certain number of the ligating rings (13). That is, after opening the pressure blocking portion (19) and closing the pressure releasing portion (18), the number of ligating rings (13) to be separated is set, and that number of ligating rings (13) are separated by the pressure applied by the manual pressure applying portion (17).

The purpose for using the pressure blocking portion (19) is to inhibit the discharge of fluids caused by residual pressure when pressure is released by the pressure releasing portion (18). This significantly reduces the fluid in the manual pressure applying portion (17) that is consumed (during each separation of the ligating rings (13). This enables the separation of a plurality of the ligating rings (13) by charging the manual pressure applying portion (17) with fluid once.

It is required that the manual pressure applying portion (17) have the ability to produce enough pressure to move two or more ligating rings (13), which are connected to the distal device (1), toward the front. In this embodiment, although it depends on the slide resistance of the inner tube (4) during movement of the ligating rings (13), a pressure of 5 kgf/cm$^2$ to 30 kgf/cm$^2$ is required when eight of the ligating rings (13) are connected. In this embodiment, the manual pressure applying portion (17) is formed by a small diameter syringe or an inflation syringe. With fluid charged in the cylinder, a piston is moved manually to compress the fluid and produce positive pressure.

The volume of the syringe must be sufficient for separating the set number of ligating rings (13) and the cylinder diameter must be selected to correspond to the user's strength, since a larger cylinder diameter requires more pressurizing force.

Although the pressure releasing portion (18) and the pressure blocking portion (19) is not limited to any particular structure, the present embodiment uses an electromagnetic valve. The electromagnetic valve is required to be capable of sufficiently resisting the interior pressure produced in the fluid circuit and to have a response time that satisfies the requirements for the operating time of the controller (10). It is preferred that the electromagnetic valve of this embodiment have an operational pressure range of 10 kgf/cm$^2$ or more, and more preferably, 20 kgf/cm$^2$ or more, and that the response time be 5 ms or less, and more preferably, 2 ms or less. Further, it is required that the employed fluid resist corrosion and that the fluid circuit be formed from a material that resists corrosion.

If there is a possibility that the interior of the electromagnetic valve may be corroded by the employed fluid, a pinch valve having a DC solenoid or the like capable of connecting the fluid tube (9) from the exterior may be used as the pressure releasing portion (18) and the pressure blocking portion (19). In this case, the same operational pressure range and response time as described above are required.

When using a liquid as the fluid, if the electromagnetic valve is used when charging the fluid prior to usage, the lands and pits of the interior passage may result in residual air depending on the selected magnetic valve and interfere with the required direct pressure fluctuation measurement. However, since the fluid passage of the pinch valve is the fluid tube (9) itself, there is no residual air.

The waveform processing portion (15) is required to have a response time that satisfies the operation time of the controller (10). In this embodiment, the waveform processing portion (15) is formed by a differentiating circuit and a comparator circuit. The voltage input by the pressure fluctuation measuring portion (14) is first converted (amplified) to a voltage that is proportional to the fluctuation by the differentiating circuit, which is formed by an operational amplifier or the like, and then compared with a predetermined voltage threshold value by the comparator circuit, which is formed by an operational amplifier or the like, to generate a signal output when the threshold value is exceeded or a signal output when the threshold value is not exceeded. In the above structure, pressure drops occur in the fluid circuit when the ligating rings (13) are separated. When the fluctuation amount of the pressure exceeds the predetermined threshold value, it is determined that a ligating ring (13) has been separated, and a signal to the control portion (16) is instantaneously sent.

A microcomputer may be used as the waveform processing portion (15). In this case, the voltage input by the pressure fluctuation measuring portion (14) is AD converted by an AD converter and then input to the microcomputer. The input voltages are input continuously in constant, short time intervals, and the difference between two consecutive input voltages is computed continuously to acknowledge when the substraction value increases due to a drop in the interior pressure of the fluid circuit during separation of a ligating ring (13). This causes the separation of the ligating ring (13) to be recognized. Further, when using the microcomputer, the conditions for determining that a ligating ring (13) has been separated from the substraction value may be programmed to be limited to the substraction value obtained during an interior pressure drop of the fluid circuit. This distinguishes electrical noise from interior pressure drops that occur when the ligating rings (13) slide in the distal device (1) and results in an instantaneous signal to the control portion (16) without erroneous actions.

The control portion (16) is also required to have a response time that satisfies the operation time of the controller (10) In this embodiment, a microcomputer or a sequencer capable of high speed processing is employed. That is, in this embodiment, the number of separated ligating rings (13) is stored through digital input or the like based on a prestored operation program. A signal indicating separation of the ligating rings (13) is input by the waveform processing portion (15). At least a function for outputting a signal to the pressure releasing portion (18) to open the pressure releasing portion (18) when the number of separated ligating rings (13) reaches a predetermined value is provided. The control portion (16) may be a circuit formed by only logic circuits, transistors, or the like, and do not have to employ a microcomputer or a sequencer. The separated number of ligating rings (13) may be counted by an internal counter or a counter attached externally, if a sequencer is used, or through internal subtractions or the like executed by a program, if a microcomputer is used.

Embodiment of Automatic Pressure Application

An example of performing pressure application automatically will now be discussed. In this successive ligation kit, the driver (11) shown in FIGS. 10 to 13 has a pressure adjusting section, which includes a pressure fluctuation measuring portion (13), a waveform processing portion (15), a control portion (16), an automatic pressure applying portion (20), and a pressure releasing portion (18). The connection of the pressure fluctuation measuring portion (14), the automatic pressure applying portion (20), and the pressure releasing portion (18) are not limited in any manner and may be connected or arranged as shown in FIG. 10 to FIG. 13.

Figure 10:
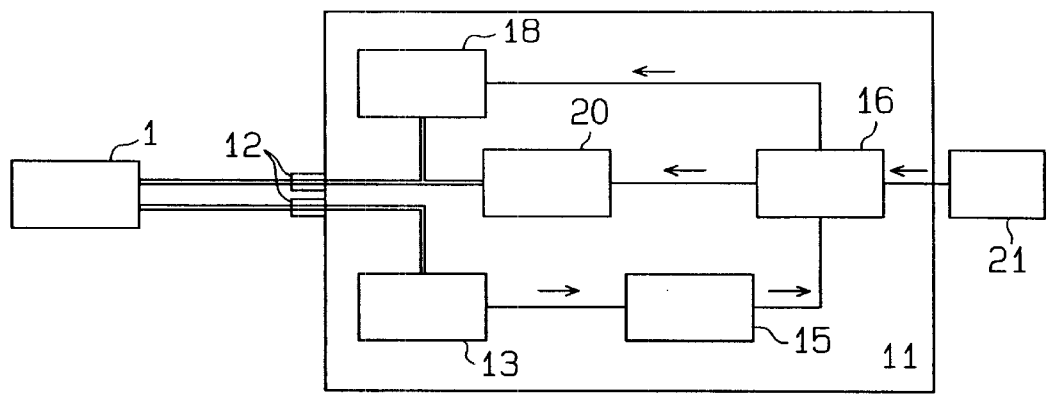

In the example of the controller (10) shown in FIG. 10, two of the fluid tubes (9) connected to the hermetic space (8) are attached to the distal device.(1). One end of the first fluid tube (9) is connected to the distal device (1), while the other end is connected to the pressure fluctuation measuring portion (14). One end of the second fluid tube (9) is connected to the distal device (1), while the other end is connected to the automatic pressure applying portion (20) and the pressure releasing portion (18).

Figure 11:
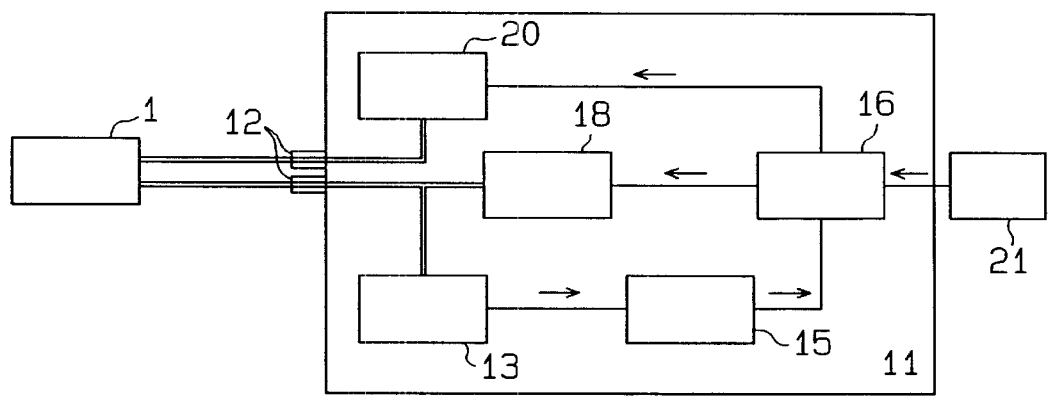

In the example of the controller (10) shown in FIG. 11, two of the fluid tubes (9) connected to the hermetic space (8) are attached to the distal device (1). One end of the first fluid tube (9) is connected to the distal device (1), while the other end is connected to the pressure fluctuation measuring portion (14) and the pressure releasing portion (18). One end of the second fluid tube (9) is connected to the distal device (1), while the other end is connected to the automatic pressure applying portion (20).

Figure 12:
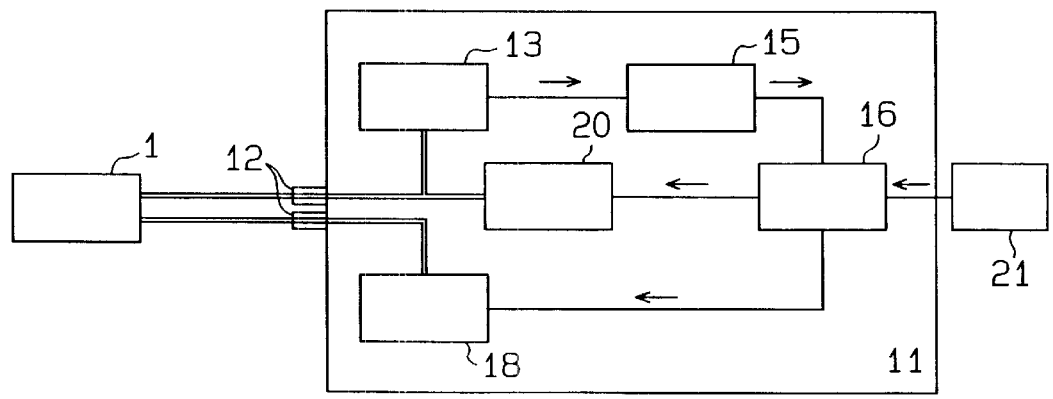

In the example of the controller (10) shown in FIG. 12, two of the fluid tubes (9) connected to the hermetic space (8) are attached to the distal device (1). One end of the first fluid tube (9) is connected to the distal device (1), while the other end is connected to the pressure releasing portion (18). One end of the second fluid tube (9) is connected to the distal device (1), while the other end is connected to the pressure fluctuation measuring portion (14) and the automatic pressure applying portion (20).

Figure 13:
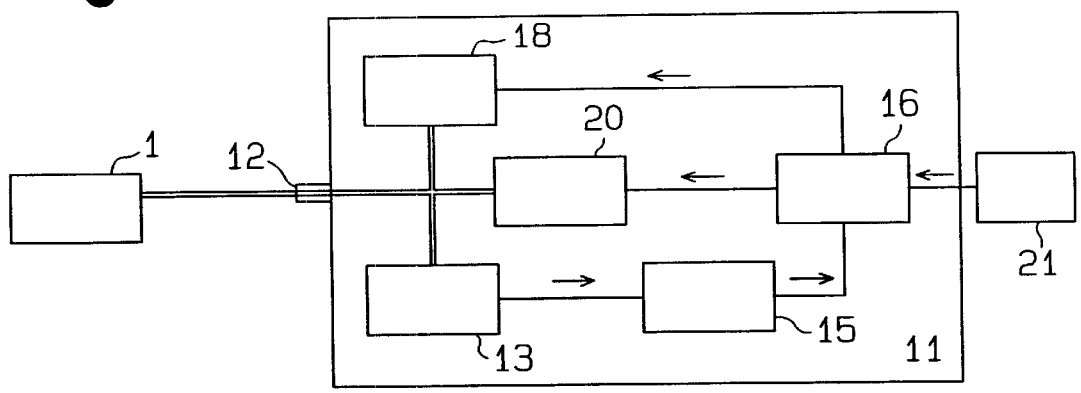

In the example of the controller (10) shown in FIG. 13, one of the fluid tubes (9) connected to the hermetic space (8) is attached to the distal device (1). One end of the fluid tube (9) is connected to the distal device (1), while the other end is connected to the automatic pressure applying portion (20) and the pressure releasing portion (18).

The control portion (16) is electrically connected to the waveform processing portion (15), the pressure releasing portion (18), and the automatic pressure applying portion (20). The waveform processing portion (15) is electrically connected to the pressure fluctuation measuring portion (14).

The operation of the successive ligation kit, which includes the driver (11) and the distal device (1) will now be discussed. The number of ligating rings (13) that are to be separated are first input to and stored in the control portion (16). A user of the kit then uses an external switch (21), which is electrically connected to the control portion (16), to input a command signal to the control portion (16) and ligate a lesion. This sends a signal from the control portion (16) to the automatic pressure applying portion (20). In response to the signal, the automatic pressure applying portion (20) produces sufficient positive pressure for driving the slide tube (4) and conveys the positive pressure to the hermetic space (8) in the distal device (1) through the fluid tube (9) and the pressure blocking portion (19), which is in an opened state.

In this state, since the pressure releasing portion, (18) and the pressure fluctuation measuring portion (14), which are controlled by the control portion (16), are closed from the exterior, the interior pressure of the hermetic space (8) in the distal device (1) increases. As a result, the slide tube (4) is moved toward the front of the distal device by the seal ring (7). Simultaneously, the plurality of the ligating rings (13) are pushed together by the slide tube (4) and start to move toward the front of the distal device (1). At this time, changes in the interior pressure of the fluid circuit, which is connected to the hermetic space (8), are constantly measured by the pressure fluctuation measuring portion (14). When the frontmost ligating ring (13) passes by the frontmost portion of the inner tube (5), the first ligating ring (13) is separated from the distal device (1).

The load of the slide tube (4) that pushes the ligating rings (13) decreases momentarily and causes the interior pressure of the fluid circuit to drop within a short period of time. Further continuation of the pressure application separates the second and subsequent ligating rings (13). A pressure drop occurs during each separation. The pressure fluctuation waveform resulting from the pressure drop is converted to an electrical waveform by the pressure fluctuation measuring portion (14) and input to the waveform processing portion (15). The waveform processing portion (15) performs waveform processing of the input electrical waveform and outputs to the control portion (16) a signal indicating a pressure drop at substantially the same time as the pressure drop in accordance with the number of separations of the ligating rings (13). The control portion (16) counts the number of separations and outputs a control signal to the pressure releasing portion (18) and the automatic pressure applying portion (20) when the number of separations reaches a prestored value.

Consequently, the pressure releasing portion (18) enters an opened state and releases the interior pressure of the fluid circuit to the exterior, and the pressure applying portion (20) stops pressurizing the circuit. This decreases the interior pressure in the circuit in a sudden manner and stops the movement of the slide tube (4), stops the movement of the ligating rings (13) subsequent to the last ring of the set number of the separated rings, and stops the separation. To perform ligation again at another lesion, the above operation is repeated to separate a certain number of the ligating rings (13). That is, after closing the pressure releasing portion (18), the number of ligating rings (13) that are to be separated is set. A command signal for ligating the legion with the ligating rings (13) is input to the control portion (16). Accordingly, that number of ligating rings (13) are separated.

The operation speed required for the controller (10) is limited by the time necessary from when the final ligating ring (13) of the set number of separated ligating rings (13) for a single treatment is separated until the first ligating ring (13) of the set number of separated ligating rings (13) of the next treatment is separated. In this embodiment, the necessary time is 50 ms to 200 ms. Thus, it is required that the operation time for the procedures occuring from when the final ligating ring (13) of the first treatment is separated to when the first ligating ring (13) of the next treatment stops be 50 ms or less.

It is required that the automatic pressure applying portion (20) have the ability to produce enough pressure for moving two or more of the ligating rings (13), which are connected to the distal device (1), toward the front. In this embodiment, although it depends on the slide resistance of the inner tube (4) during movement of the ligating rings (13), a pressure of 5 kgf/cm$^2$ to 30 kgf/cm$^2$ is required when eight of the ligating rings (13) are connected. In this embodiment, the automatic pressure applying portion (20) is formed by a piston pressure applying device that includes a cylinder and a piston. The pressure applying device is connected to the fluid circuit. In a pressurizing space defined by the inner wall of the cylinder and the piston, the piston is moved in a direction that decreases the volume of the piston to compress the fluid and produce positive pressure.

The power source for moving the piston must be capable of resisting loads produced during the application of pressure. Although this embodiment is not limited to any particular structure, a linear motor, which generates a sufficient amount of torque and converts the rotational movement produced by the motor to linear movement, is employed. When using the piston pressure applying device, the pressure releasing portion (18) may be used together to decrease the interior pressure of the fluid circuit in a sudden manner immediately after separation of the ligating rings (13). A pressure decrease may also be achieved by moving the piston by a constant distance in a direction that increases the volume of the pressurizing space by means of control by the control portion (16). A compressor may be used as the automatic pressure applying portion (20) instead of the piston pressure applying device.

Although the pressure releasing. portion (18) is not limited to any particular structure, the present embodiment uses an electromagnetic valve. The electromagnetic valve is required to be capable of sufficiently resisting the interior pressure produced in the fluid circuit and to have a response time that satisfies the requirements for the operating time of the driver (11). It is preferred that the electromagnetic valve of this embodiment have an operational pressure range of 10 kgf/cm$^2$ or more, and more preferably, 20 kgf/cm$^2$ or more, and a response time of 5 ms or less, and more preferably, 2 ms or less. Further, it is required that the employed fluid resist corrosion and that the fluid circuit be formed from a material that resists corrosion.

If there is a possibility that the interior of the electromagnetic valve may be corroded by the employed fluid, a pinch valve having a DC solenoid or the like capable of connecting the fluid tube (9) from the exterior may be used as the pressure releasing portion (18). In this case, the same operational pressure range and response time as described above are required.

When using a liquid as the fluid, if the electromagnetic valve is used when charging the fluid prior to usage, the lands and pits of the interior passage may result in residual air depending on the selected magnetic valve and interfere with the required direct pressure fluctuation measurement. However, since the fluid passage of the pinch valve is the fluid tube (9) itself, there is no residual air.

The waveform processing portion (15) is required to have a response time that satisfies the operation time of the driver (11). In this embodiment, the waveform processing portion (15) is formed by a differentiating circuit and a comparator circuit. The voltage input by the pressure fluctuation measuring portion (14) is first converted (amplified) to a voltage that is proportional to the fluctuation by the differentiating circuit, which is formed by an operational amplifier or the like, and then compared with a predetermined voltage threshold value by the comparator circuit, which is formed by an operational amplifier or the like, to generate a signal output when the threshold value is exceeded or a signal output when the threshold value is not exceeded.

In the above structure, pressure drops occur in the fluid circuit when the ligating rings (13) are separated. When the fluctuation amount of the pressure exceeds the predetermined threshold value, it is determined that a ligating ring (13) has been separated and a signal to the control portion (16) is instantaneously sent.

A microcomputer may be used as the waveform processing portion (15). In this case, the voltage input by the pressure fluctuation measuring portion (14) is AD converted by an AD converter and then input to the microcomputer. The input voltages are input continuously in constant, short time intervals, and the difference between two consecutive input voltages (substraction value) is computed continuously. Acknowledgement of an increase in the substraction value resulting from a drop in the interior pressure of the fluid circuit when a ligating ring (13) is separated causes the separation of the ligating ring (13) to be recognized. Further, when using the microcomputer, the conditions for determining that a ligating ring (13) has been separated from the substraction value may be programmed to be limited to the substraction value obtained during an interior pressure drop of the fluid circuit. This distinguishes electrical noise from interior pressure drops that occur when the ligating rings (13) slide in the distal device (1) and results in an instantaneous signal to the control portion (16) without erroneous actions.

The control portion (16) is also required to have a response time that satisfies the operation time of the driver (11). In this embodiment, a microcomputer or a sequencer capable of high speed processing is employed. That is, in this embodiment, the number of separated ligating rings (13) is stored through digital input or the like based on a prestored operation program. A signal indicating separation of the ligating rings (13) is input by the waveform processing portion (15). At least a function for outputting a signal to the pressure releasing portion (18) to open the pressure releasing portion (18) when the number of separated ligating rings (13) reaches a predetermined value is provided. The control portion (16) may be a circuit formed by only logic circuits, transistors, or the like, and do not have to employ a microcomputer or a sequencer. The separated number of ligating rings (13) may be counted by an internal counter or a counter attached externally, if a sequencer is used, or through internal subtractions or the like executed by a program, if a microcomputer is used.

Further Embodiment of Automatic Pressure Application

As another example of performing pressure application automatically, the driver (11) may be formed as shown in FIGS. 14 to 17. In this successive ligation kit, the driver (11) includes a pressure fluctuation measuring portion (14) a waveform processing portion (15), a control portion (16), an automatic pressure applying portion (20), a pressure releasing portion (18), and a pressure blocking portion (19). The connection of the pressure fluctuation measuring portion (14), the automatic pressure applying portion (20), the pressure releasing portion (18), the pressure blocking portion (19) is not limited in any manner and may be connected or arranged as shown in FIG. 14 to FIG. 17.

Figure 14:
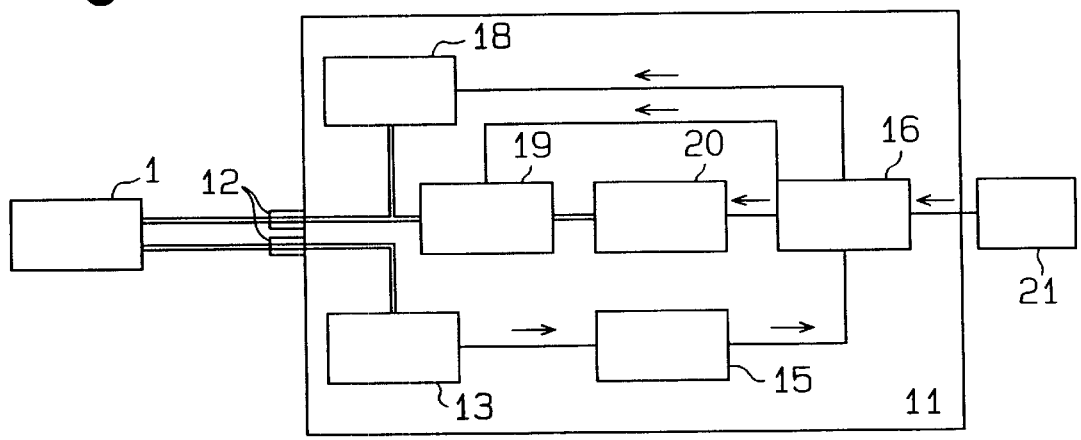

In the example of the driver (11) shown in FIG. 14, two of the fluid tubes (9) connected to the hermetic space (8) are attached to the distal device (1). One end of the first fluid tube (9) is connected to the distal device (1), while the other end is connected to the pressure fluctuation measuring portion (14). One end of the second fluid tube (9) is connected to the distal device (1), while the other end is connected to the automatic pressure applying portion (20) and the pressure releasing portion (18). The pressure blocking portion (19) is connected between the automatic pressure applying portion (20) and the pressure releasing portion (18).

Figure 15:
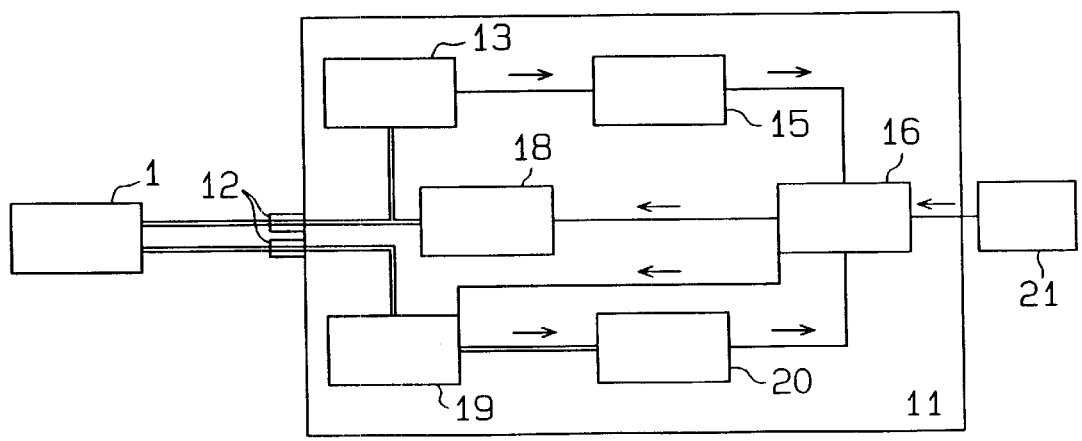

In the example of the driver (11) shown in FIG. 15, two of the fluid tubes (9) connected to the hermetic space (8) are attached to the distal device (1). One end of the first fluid tube (9) is connected to the distal device (1), while the other end is connected to the pressure fluctuation measuring portion (14) and the pressure releasing portion (18). One end of the second fluid tube (9) is connected to the distal device (1), while the other end is connected to the automatic pressure applying portion (20). The pressure blocking portion (19) is connected between the automatic pressure applying portion (20) and the distal device (1).

Figure 16:
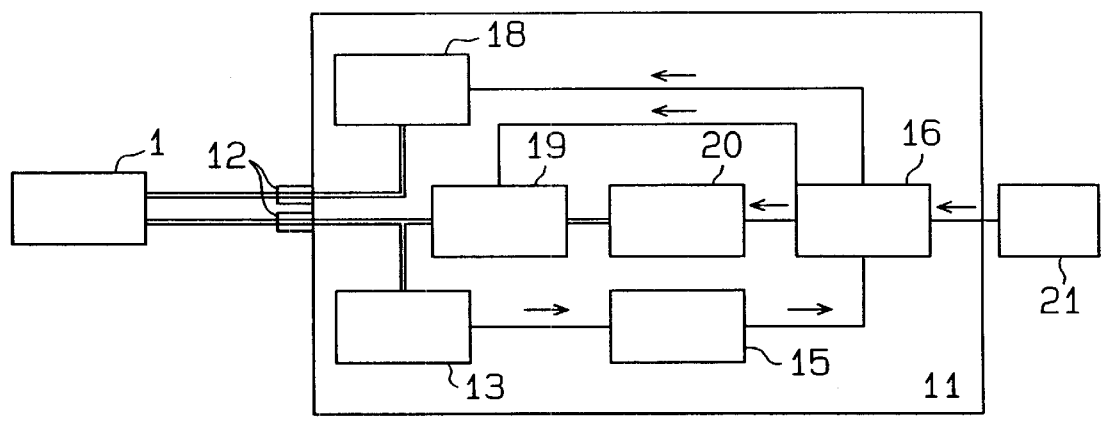

In the example of the driver (11) shown in FIG. 16, two of the fluid tubes (9) connected to the hermetic space (8) are attached to the distal device (1). One end of the first fluid tube (9) is connected to the distal device (1), while the other end is connected to the pressure releasing portion (18). One end of the second fluid tube (9) is connected to the distal device (1), while the other end is connected to the pressure fluctuation measuring portion (14) and the automatic pressure applying portion (20). The pressure blocking portion (19) is connected between the automatic pressure applying portion (20) and the pressure fluctuation measuring portion (14).

Figure 17:
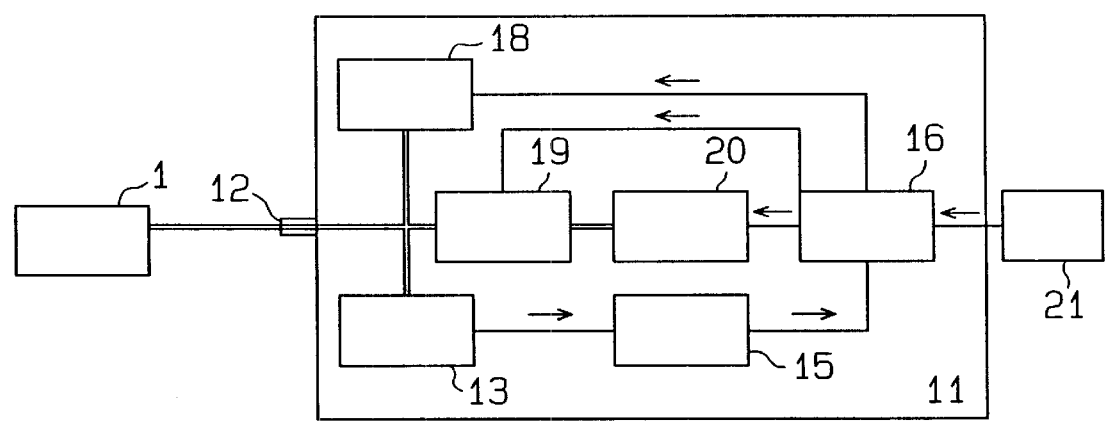

In the example of the driver (11) shown in FIG. 17, one of the fluid tubes (9) connected to the hermetic space (8) is attached to the distal device (1). One end of the fluid tube (9) is connected to the distal device (1), while the other end is connected to the pressure fluctuation measuring portion (14,) the automatic pressure applying portion (20), and the pressure releasing portion (18). The pressure blocking portion (19) is connected between the pressure fluctuation measuring portion (14) or the pressure releasing portion (18) and the automatic pressure applying portion (20).

The control portion (16) is electrically connected to the waveform processing portion (15), the automatic pressure applying portion (20), the pressure releasing portion (18), and the pressure blocking portion (19). The waveform processing portion (15) is electrically connected to the pressure fluctuation measuring portion (14).

The operation of the successive ligation kit, which includes the driver (11) and the distal device (1) will now be discussed. The number of ligating rings (13) that are to be separated are first input to and stored in the control portion (16). A user of the kit then uses an external switch (21), which is electrically connected to the control portion (16), to input a command signal to the control portion (16) for ligating a lesion. This sends a signal from the control portion (16) to the automatic pressure applying portion (20). In response to the signal, the automatic pressure applying portion (20) produces sufficient positive pressure for driving the slide tube (4) and conveys the positive pressure to the hermetic space (8) in the distal device (1) through the fluid tube (9) and the pressure blocking portion (19), which is in an opened state.

In this state, since the pressure releasing portion (18) and the pressure fluctuation measuring portion (14), which are controlled by the control portion (16), are closed from the exterior and the pressure blocking portion (19) is opened, the interior pressure of the hermetic space (8) in the distal device (1) increases. As a result, the slide tube (4) is moved toward the front of the distal device by the seal ring (7). Simultaneously, the plurality of the ligating rings (13) are pushed together by the slide tube (4) and start to move toward the front of the distal device (1). At. this time, changes in the interior pressure of the fluid circuit, which is connected to the hermetic space (8), are constantly measured by the pressure fluctuation measuring portion (14). When the frontmost ligating ring (13) passes by the frontmost portion of the inner tube (5), the first ligating ring (13) is separated from the distal device (1).

The load of the slide tube (4) that pushes the ligating rings (13) decreases momentarily and causes the interior pressure of the fluid circuit to drop within a short period of time. Further continuation of the pressure application separates the second and subsequent ligating rings (13). A pressure drop occurs during each separation. The pressure fluctuation waveform resulting from the pressure drop is converted to an electrical waveform by the pressure fluctuation measuring portion (14) and input to the waveform processing portion (15). The waveform processing portion (15) performs waveform processing of the input electrical waveform and outputs to the control portion (16) a signal indicating a pressure drop at substantially the same time as the pressure drop in accordance with the number of separations of the ligating rings (13). The control portion (16) counts the number of separations and outputs a control signal to the pressure releasing portion (18), the pressure blocking portion (19), and the automatic pressure applying portion (20) when the number of separations reaches a prestored value.

Consequently, the pressure releasing portion (18) enters an opened state and releases the interior pressure of the fluid circuit to the exterior. The automatic pressure applying portion (20) stops pressurizing the circuit and the pressure blocking portion (19) enters a closed state. Thus, the application of pressure with the fluid from the automatic pressure applying portion (20) is stopped. This decreases the interior pressure in the circuit in a sudden manner and stops the movement of the slide tube (4), stops the movement of the ligating rings (13) subsequent to the last ring of the set number of the separated rings, and stops moving and is not separated. To perform ligation again at another lesion, the above operation is repeated to separate a certain number of the ligating rings (13) that are in a stopped state. That is, after opening the pressure blocking portion (19) and closing the pressure releasing portion (18), the number of ligating rings (13) to be separated is set. The external switch (21) is used to input to the control portion a command signal for ligating the lesion with the ligating rings (13) and separating a certain number of the ligating rings (13), accordingly.

The purpose for using the pressure blocking portion (19) is to inhibit the discharge of fluids caused by residual pressure when pressure is released by the pressure releasing portion (18). This significantly reduces the fluid in the automatic pressure applying portion (20) that is consumed during each separation of the ligating rings (13). This enables the separation of a plurality of the ligating rings (13) by charging the automatic pressure applying portion (20) with fluid once.

The operation speed required for the driver (11) is limited by the time necessary from when the final ligating ring (13) of the set number of separated ligating rings (13) for a single treatment is separated until the first ligating ring (13) of the set number of separated ligating rings (13) of the next treatment is separated. In this embodiment, the necessary time is 50 ms to 200 ms. Thus, it is required that the operation time for the procedures occuring from when the final ligating ring (13) of the first treatment is separated to when the first ligating ring (13) of the next treatment stops be 50 ms or less.

It is required that the automatic pressure applying portion (20) have the ability to produce enough pressure for moving two or more of the ligating rings (13), which are connected to the distal device (1), toward the front. In this embodiment, although it depends on the slide resistance of the inner tube (4) during movement of the ligating rings (13), a pressure of 5 kgf/cm$^2$ to 30 kgf/cm$^2$ is required when eight of the ligating rings (13) are connected. In this embodiment, the automatic pressure applying portion (20) is formed by a piston pressure applying device that includes a cylinder and a piston. The pressure applying device is connected to the fluid circuit. In a pressurizing space encompassed by the inner wall of the cylinder and the piston, the piston is moved in a direction that decreases the volume of the piston to compress the fluid and produce positive pressure.

The power source for moving the piston must be capable of resisting loads produced during the application of pressure. Although this embodiment is not limited to any particular structure, a linear motor, which generates a sufficient amount of torque and converts the rotational movement produced by the motor to a linear movement, is employed. When using the piston pressure applying device, the pressure releasing portion (18) may be used together to decrease the interior pressure of the fluid circuit in a sudden manner immediately after separation of the ligating rings (13). The pressure may also be decreased by moving the piston by a constant distance in a direction that increases the volume of the pressurizing space by means of control by the control portion (16). A compressor may be used as the automatic pressure applying portion (20) instead of the piston pressure applying device.

Although the pressure releasing portion (18) and the pressure blocking portion (19) are not limited to any *particular structure, the present embodiment uses an electromagnetic valve. The electromagnetic valve is required to be capable of sufficiently resisting the interior pressure produced in the fluid circuit and to have a response time that satisfies the requirements for the operating time of the driver (15). It is preferred that the electromagnetic valve of this embodiment have an operational pressure range of 10 kgf/cm$^2$ or more, and more preferably, 20 kgf/cm$^2$ or more, and that the response time be 5 ms or less, and more preferably, 2 ms or less. Further, it is required that the employed fluid resist corrosion and that the fluid circuit be formed from a material that resists corrosion.

If there is a possibility that the interior of the electromagnetic valve may be corroded by the employed fluid, a pinch valve having a DC solenoid or the like capable of connecting the fluid tube (9) from the exterior may be used as the pressure releasing portion (18) and the pressure blocking portion (19). In this case, the same operational pressure range and response time as described above are required.

When using a liquid as the fluid, if the electromagnetic valve is used when charging the fluid prior to usage, the lands and pits of the interior passage may result in residual air depending on the selected magnetic valve and interfere with the required direct pressure fluctuation measurement. However, since the fluid passage of the pinch valve is the fluid tube (9) itself, there is no residual air.

The waveform processing portion (15) is required to have a response time that satisfies the operation time of the driver (11). In this embodiment, the waveform processing portion (15) is formed by a differentiating circuit and a comparator circuit. The voltage input by the pressure fluctuation measuring portion (14) is first converted to a voltage that is proportional to the fluctuation by the differentiating circuit, which is formed by an operational amplifier or the like, and then compared with a predetermined voltage threshold value by the comparator circuit, which is formed by an operational amplifier or the like, to generate a signal output when the threshold value is exceeded or a signal output when the threshold value is not exceeded.

In the above structure, pressure drops occur in the fluid circuit when the ligating rings (13) are separated. When the fluctuation amount of the pressure exceeds the predetermined threshold value, it is determined that a ligating ring (13) has been separated and a signal to the control portion (16) is instantaneously sent.

A microcomputer may be used as the waveform processing portion (15). In this case, the voltage input by the pressure fluctuation measuring portion (14) is AD converted by an AD converter and then input to the microcomputer. The input voltages are input continuously in constant, short time intervals, and the difference between two consecutive input voltages (substraction value) is computed continuously. Acknowledgement of an increase in the substraction value resulting from a drop in the interior pressure of the fluid circuit when a ligating ring (13) is separated causes the separation of the ligating ring (13) to be recognized. Further, when using the microcomputer, the conditions for determining that a ligating ring (13) has been separated from the substraction value may be programmed to be limited to the substraction value obtained during an interior pressure drop of the fluid circuit. This distinguishes electrical noise from interior pressure drops that occur when the ligating rings (13) slide in the distal device (1) and results in an instantaneous signal to the control portion (16) without erroneous actions.

The control portion (16) is also required to have a response time that satisfies the operation time of the driver (11). In this embodiment, a microcomputer or a sequencer capable of high speed processing is employed. That is, in this embodiment, the number of separated ligating rings (13) is stored through digital input or the like based on a prestored operation program. A signal indicating separation of the ligating rings (13) is input by the waveform processing portion (15). At least a function for outputting a signal to the pressure releasing portion (18) to open the pressure releasing portion (18) when the number of separated ligating rings (13) reaches a predetermined value is provided. The control portion (16) may be a circuit formed by only logic circuits, transistors, or the like, and do not have to employ a microcomputer or a sequencer. The separated number of ligating rings (13) may be counted by an internal counter or a counter attached externally, if a sequencer is used, or through internal subtractions or the like executed by a program, if a microcomputer is used.

Embodiments of Each Kit Portion

Although the pressure fluctuation measuring portion (14) is not limited to any particular structure as long as the fluctuation of pressure in the fluid circuit can be detected, a first embodiment employs a pressure sensor. When employing the pressure sensor, it is required that the pressure sensor be capable of sufficiently resisting the interior pressure produced in the fluid circuit, having a resolution that sufficiently recognizes the interior pressure drops, and having a response time that satisfies the operation time of the driver (15). In this embodiment, it is preferred that the operation pressure range be 10 kgf/cm$^2$ to 50 kgf/cm$^2$, the resolution for a voltage output type sensor be 0.001V or less, and the response time be 5 ms or less.

Figure 18:
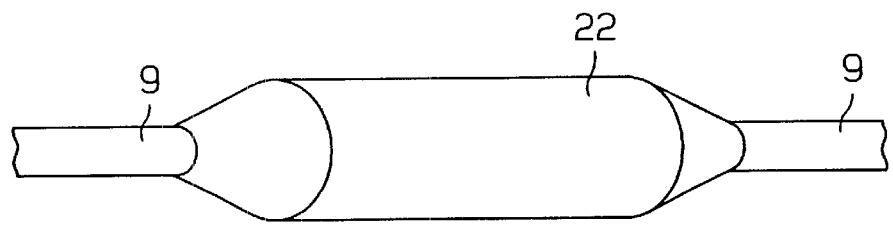
FIG. 18 is an external view showing a pressure receiving balloon according to an embodiment of the present invention.
Figure 19:
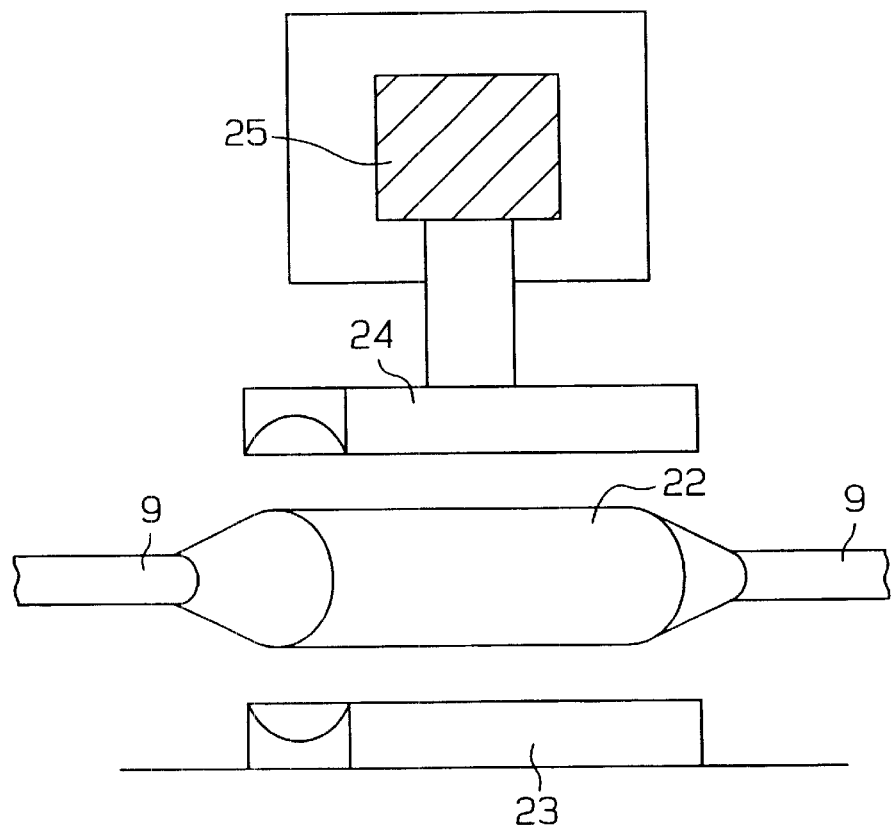
FIG. 19 is a schematic view showing the entire structure of the pressure receiving balloon and the load sensor with the pressure receiving balloon in a state prior to being fixed.
Figure 20:
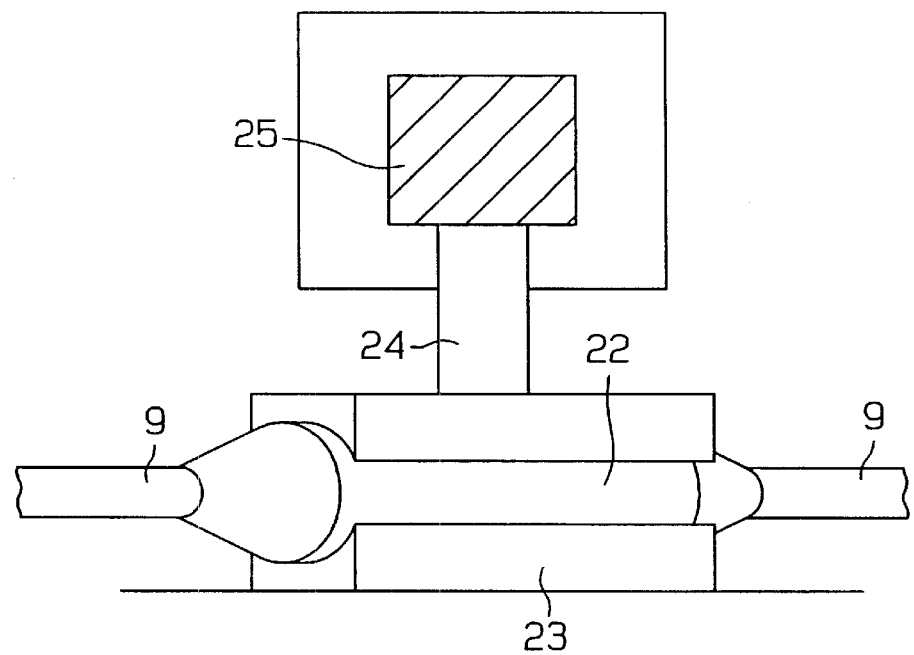
FIG. 20 is a schematic view showing the entire structure of the pressure receiving balloon and the load sensor with the pressure receiving balloon in a state subsequent to being fixed.

In a second embodiment of the pressure fluctuation measuring portion (14), a pressure receiving balloon (22) communicated with the fluid tubes (9) in the interior. As shown in FIG. 18, the front and rear of the pressure receiving balloon (22) is connected to the fluid tubes (9). Further, is shown in FIGS. 19 and 20, the pressure receiving balloon (22) is held between the balloon holding portion (23) and a probing portion (24). The probing portion (24) is formed by a piezoelectric element or the like and directly connected to a load sensor (25), which converts a load value to an electric signal.

The operation in which pressure fluctuation in the distal device (1) is detected will now be discussed. Since the distal device (1) is communicated with the pressure receiving balloon (22), the pressure fluctuation of the distal device (1) is substantially synchronized with the pressure fluctuation of the pressure receiving balloon (22). The pressure receiving balloon (22) expands and contracts in accordance with fluctuations of the interior pressure and presses the load sensor (25) by means of the probing portion (24) with the applied load fluctuation in synchronism with the interior pressure fluctuation. Since the load sensor (25) senses the load fluctuation, pressure fluctuation in the distal device can be indirectly sensed. Thus, pressure drops, which occur when the ligating rings (13) are separated, are output electrically by the load sensor (25) as load value decreases that take place at the same timing as the pressure drops and can thus be sensed.

Although the material of the pressure receiving balloon (22) is not limited, it is preferred that the material be urethane resin, soft vinyl chloride resin, or polyethylene terephthalate. It is also preferred that the pressure receiving balloon (22) be tapered (funnel-like) at the portions connected to the fluid tubes (9) so that if a liquid is used as the fluid, air does not reside when charging the liquid prior to usage. Although the taper angle is not limited, 5° to 30° is recommended. Since the balloon reaches the same pressure value as the distal device (1), it is required to have a thickness that avoids rupture when expanded and have the same pressure resisting property as the distal device (1). In this embodiment, the thickness is about 0.05 mm to 0.3 mm. It is preferred that the diameter of the pressure receiving balloon (22) be 1 mm to 5 mm since it must respond to pressure fluctuations with subtlety and be able to expand and contract.

The load sensor (25) is formed by a piezoelectric element or the like and can thus convert the load applied to the sensor to an electric variable. It is optimal that the sensor be of a type that converts a load value to a voltage value. However, a type that outputs the load values in the form of internal resistance values or current values may also be employed. It is required that the load sensor (25) be able to measure at least the maximum load produced by the pressure receiving balloon (22). In this embodiment, a load of 1 to 5 kgf can be measured. The output requirements for a voltage output type are the resolution being 0.001V or less, the response time being 5 ms or less and more preferably 3 ms or less.

Figure 21:
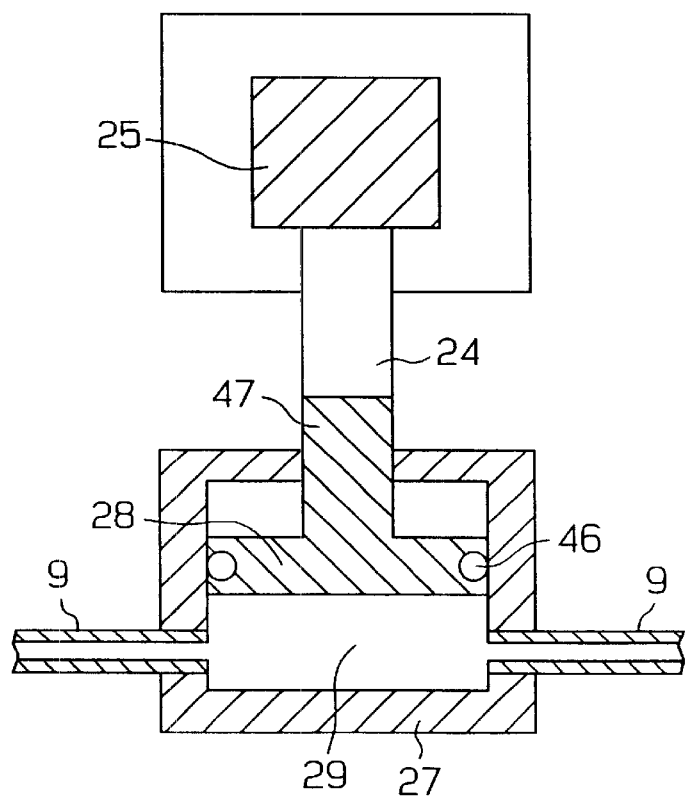
FIG. 21 is a schematic view showing the entire structure of a pressure receiving piston and the load sensor according to an embodiment of the present invention.

In a third embodiment of the pressure fluctuation measuring portion (14), a pressure receiving piston (26) is connected to the fluid tubes (9). As shown in FIG. 21, the pressure receiving piston (26) has a piston body (28) that slides in one direction in a cylinder case (27). At least two or more of the fluid tubes (9) is connected to the hermetic chamber (29) partitioned by the piston body (28) and the cylinder case (27). A piston ring (46) is arranged at the portion of contact between the piston body (28) and the cylinder case (27) to ensure hermetic sealing. The piston body (28) has a piston probing portion (47) extending externally from the opposite side of the hermetic chamber (29) along the sliding axis. As shown in FIG. 21, the pressure receiving piston (26) is set and used so that the piston probing portion (47) contacts a probing portion (24) of a load sensor (25), which converts load values to electric signals. The probing portion (24) of the sensor (25) is formed by a piezoelectric element or the like and directly connected to the load sensor (25).

The operation for measuring pressure fluctuation in the distal device (1) will now be described. Since the distal device (1) and the hermetic chamber (29) of the pressure receiving piston (26) are communicated, the pressure fluctuation in the distal device (1) is substantially synchronized with the pressure fluctuation in the hermetic chamber (29). The piston body (28) slides in accordance with the fluctuations of the interior pressure in the hermetic chamber (29) and presses the load sensor (25) by means of the piston probing portion (47) and the sensor probing portion (24) with a load value that is proportional to the interior pressure of the hermetic chamber (29). Since the load sensor (25) senses fluctuations of the load value, the pressure fluctuations of the distal device (1) can also be sensed. Thus, pressure drops during separation of the ligating rings (13) can be sensed as electric outputs of the load sensor (25).

Although the cylinder case (27) and the piston are not limited to be made of any material, considering the required injection molding characteristics and strength for manufacture, it is preferred that they be made of polycarbonate resin, polysulfone resin, or the like. Since the hermetic chamber (29) reaches a pressure value that is the same as the distal device (1), the chamber must have strength that obtains the same pressure resisting characteristic as the distal device (1). It is preferred that the piston ring (46) be made of silicone resin since sufficient hermetic seal, sliding resistance, wear resistance, and productivity can be provided.

The load sensor (25) is formed by a piezoelectric element or the like and can thus convert the load applied to the sensor to an electric variable. It is optimal that the sensor be of a type that converts a load value to a voltage value. However, a type that outputs the load values in the form of internal resistance values or current values may also be employed. It is required that the load sensor (25) be able to) measure at least the maximum load produced by the pressure receiving balloon (22). In this embodiment, a load of 1 to 5 kgf can be measured. The output requirements for a voltage output type are the resolution being 0.001V or less, the response time being 5 ms or less and more preferably 3 ms or less.

The cross-sectional area (28) of the piston body (28) is determined in accordance with the pressure range of the employed load sensor (25). The pressure produced in the distal device (1) may be determined based on the ratio between the cross-sectional area of the hermetic chamber (8) and the cross-sectional area of the piston body (28). In this embodiment, the ratio between the cross-sectional area of the hermetic chamber (8) and the cross-sectional area of the piston body (28) is 2:1 taking into consideration the maximum load produced at the distal device (1) and the maximum load of the load sensor (25). However, the ratio is not limited in any manner.

The fluid charged into the fluid circuit of the successive ligation kit may be any one of a gas or a liquid, and may be air when using a gas or a liquid that can easily be procured.

When using a liquid such as water or silicone oil, the level of expansion and compression is not high. This enables the behavior of pressure in the distal device (1) during the separation of the ligating rings (13) to be directly transmitted to the pressure fluctuation measuring portion (14) and prevents erroneous functioning resulting from sensing errors. However, the selected liquid must be one that does not corrode the flow passage of the fluid circuit. If water is used as the fluid, it is preferred that the metal portion of the fluid circuit that comes into contact with the water be made of stainless steel, which resists corrosion caused by water.

To produce a high pressure gas, a large volume change must occur at a pressure applying portion of a syringe or the like, which has a large diameter, a long stroke, and a large volume. Thus, an extremely large amount of force must be applied to the pressure applying portion. However, if a liquid is employed, the expansion and contraction is small. Therefore, the pressure applying portion may have a relatively small volume and a small diameter. This enables high pressure to be generated when an extremely small force is applied to the pressure applying portion.

When using a liquid, if air enters the fluid circuit connected to the pressure fluctuation measuring portion (14), the required sensitivity cannot be obtained. Thus, measures must be taken so that the fluid circuit does not contain residual air.

An embodiment that prevents air from residing in the fluid circuit is shown in FIGS. 22 to 25. The controller (10), which is shown in FIG. 6 and provided with the pressure blocking portion (19) and which performs pressure application manually to separate the ligating rings (13), is used.

Figure 22:
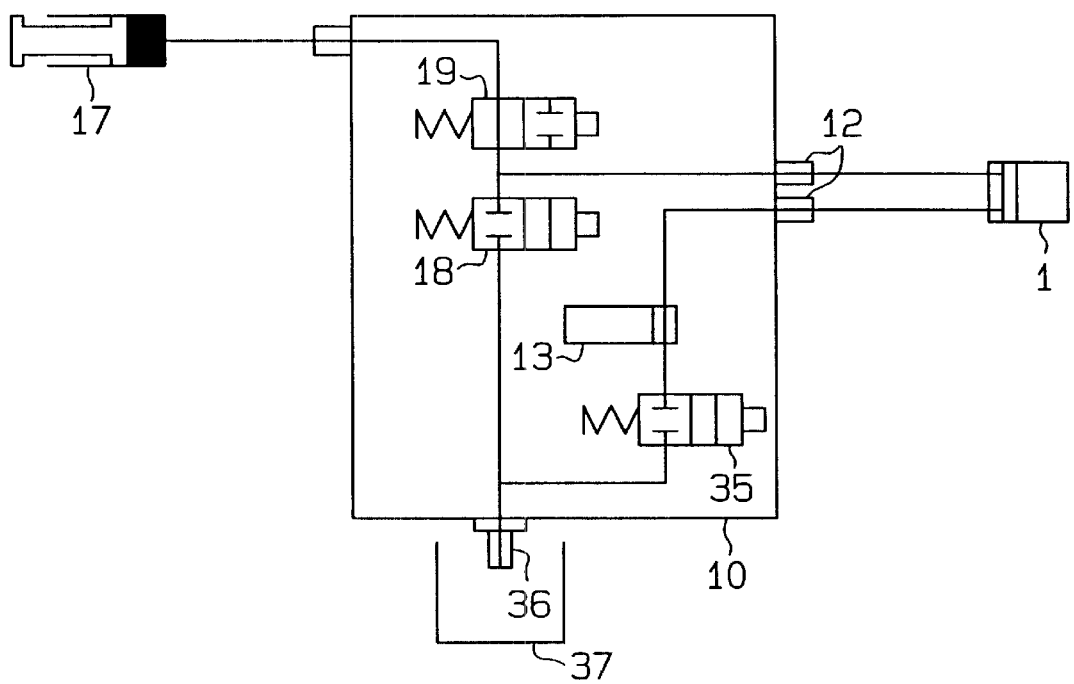
FIGS. 22 to 25 are diagrams showing a fluid circuit for charging water when using water as a fluid and showing charging procedures in the successive ligation kits according to each of the embodiments of the present invention.

In this embodiment, as shown in FIG. 22, a syringe, which serves as the manual pressure applying portion (17) is connected to an inlet of a normally opened first electromagnetic valve, which serves as the pressure blocking portion (19). The outlet of the first electromagnetic valve is connected to an inlet of a normally closed second electromagnetic valve, which serves as the pressure releasing portion (18). The fluid circuit between the outlet of the first electromagnetic valve (19) and the inlet of the second electromagnetic valve (18) and connected to the distal device (1) by the connector (12) and one of the two fluid tubes (9). The other one of the two fluid tubes (9) extends through the pressure fluctuation measuring portion (13) and is connected to the inlet of a normally closed third electromagnetic valve, which serves as a charging portion (35). The outlet of the second electromagnetic valve (18) and the outlet of the third electromagnetic valve (35) are connected to a waste liquid port (36), which is communicated with the exterior. A waste liquid collector (37) is arranged directly below the waste liquid port (36) to receive the liquid discharged from the waste liquid port (36).

Figure 23:
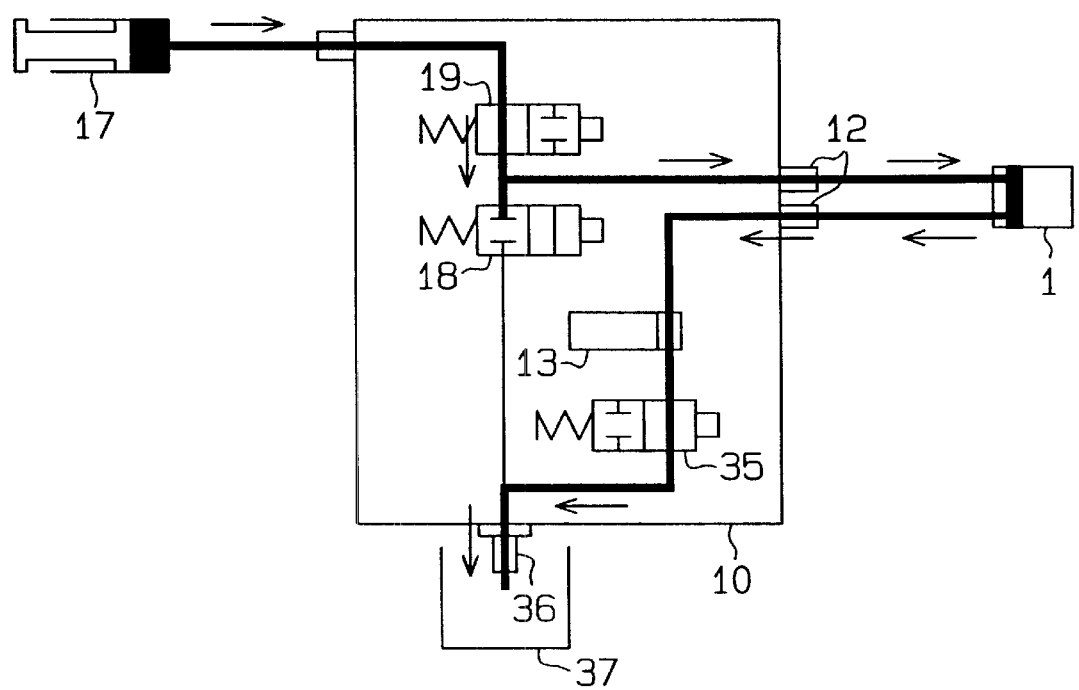
Figure 24:
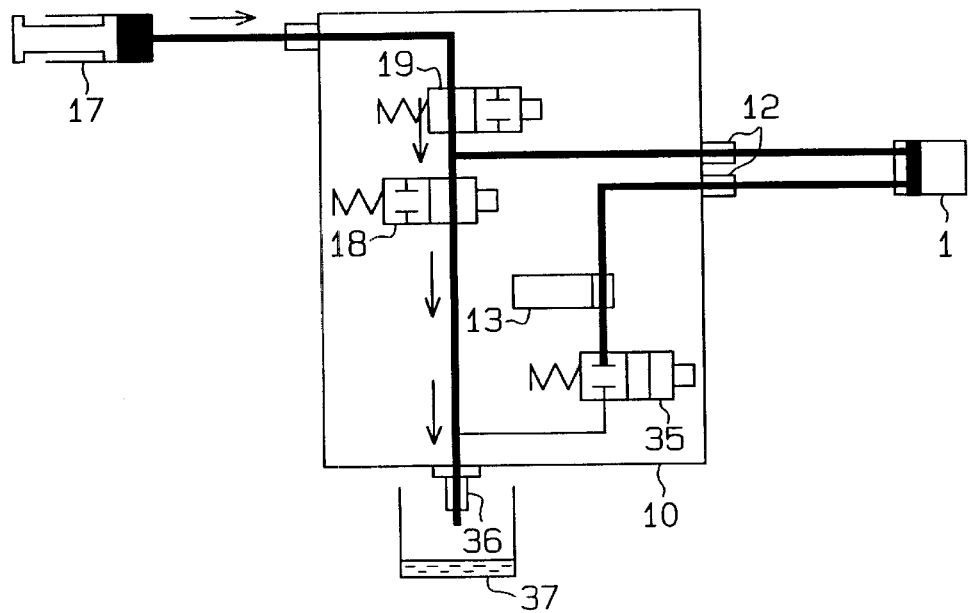
Figure 25:
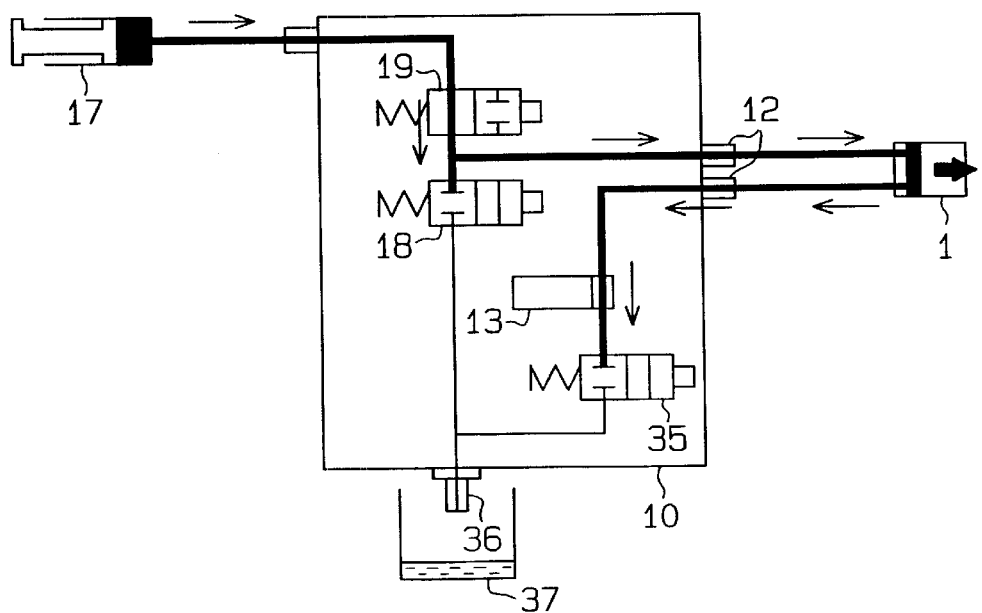

Referring to FIG. 23, during actual liquid charging, the pressure blocking portion (19) is opened, the pressure releasing portion (18) is closed, and the charging portion (35) is opened. A sufficient amount of liquid is charged by the manual pressure applying portion (17) so that the liquid (e.g., water) flows through the pressure blocking portion (19), the distal device (1), the pressure fluctuation measuring portion (14), the charging portion (35), the waste liquid port (36), and the waste liquid collector (37). The fluid circuit between the manual pressure applying portion (17), the pressure blocking portion (19), the distal device (1), the pressure fluctuation measuring portion (14), and the charging portion (35) is then filled with the liquid.

In this state, there may be air in the inlet of the pressure releasing portion (18). Thus, referring to FIG. 24, the pressure blocking portion (19) is opened, the pressure releasing portion (18) is opened, and the charging portion (35) is closed. In this state, a sufficient amount of liquid is charged by the manual pressure applying portion (17) so that the liquid (e.g., water) flows through the pressure blocking portion (19), the pressure releasing portion (18), the waste liquid port (36), and the waste liquid collector (37). This eliminates the air in the inlet of the pressure releasing portion (18) and fills it with the liquid. As a result, with reference to FIG. 25, the fluid circuit is filled with liquid. Thus, the pressure blocking portion (19) is opened, the pressure releasing portion (18) is closed, and the charging portion (35) is closed. By initiating pressure application in this state with the manual pressure applying portion (17), the pressure of the distal device (1) increases and the ligating rings (13) are separated, as described above.

For hygienic reasons, it is preferred that the distal device (1) and the fluid tubes (9), which come into contact with the patient, be disposable. In the structure of FIG. 22, only the distal device (1), the fluid tube (9), the connector (12), and the manual pressure applying portion (17) are disposable. When water, which is easily procured, is used as the fluid, bacteria may be produced in the slight amounts of water that remain in the piping of the controller (10) and the electromagnetic valve. This may lead to hygienic problems.

Figure 26:
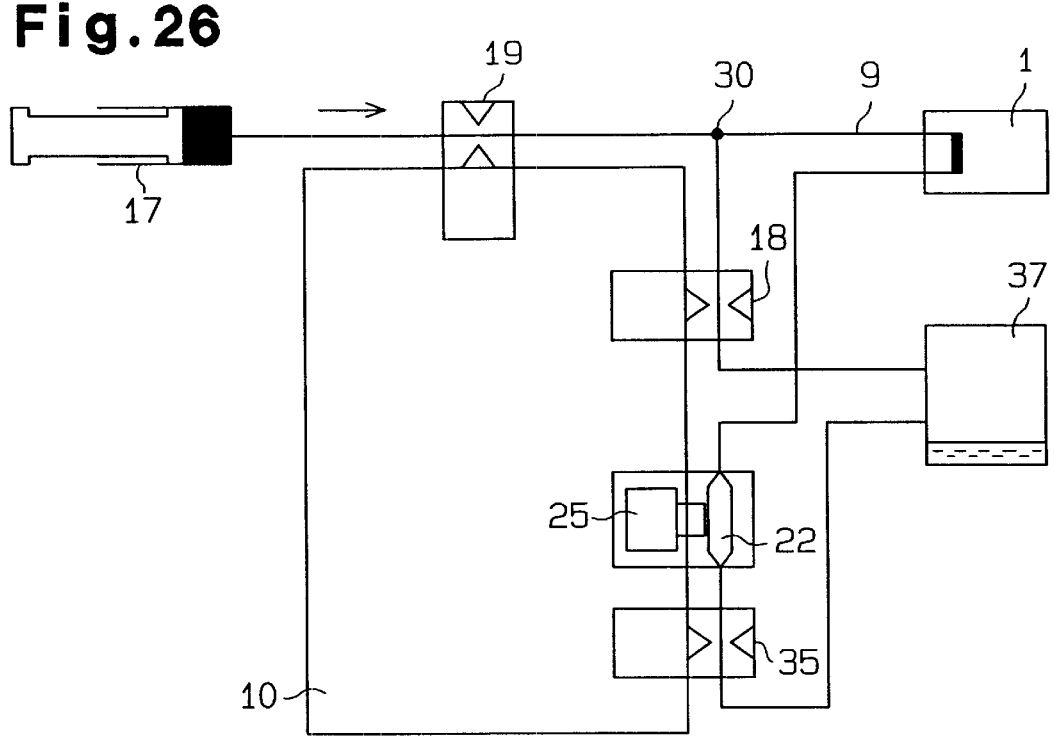
FIG. 26 is a diagram showing an embodiment using water as the fluid of a ligation kit and employing a pressure receiving balloon and a pinch valve.

Such problem is solved by an embodiment shown in FIG. 26, in which the above-mentioned pressure receiving balloon (22) is applied to the pressure fluctuation measuring portion (14) of FIG. 22 and the above-mentioned pinch valve form the pressure releasing portion (18), the pressure blocking portion (19), and the charging portion (35). In this embodiment, among the two fluid tubes (9) extending from the distal device (1), a first fluid tube (9) is connected to the manual pressure applying portion (17). A bifurcating portion (30) bifurcating the circuit is provided between the distal device (1) and the manual pressure applying portion (17) and connected to a bag-like waste liquid collector (37). Among the two fluid tubes (9) extending from the distal device (1), a second fluid tube (9) is connected to one end of the pressure receiving balloon (22). The other end of the pressure receiving balloon (22) is connected to the waste liquid collector (37). These parts define an integral disposable portion.

In the controller (10), the connecting portion of the pressure receiving balloon (22) and the head portions of the pressure releasing portion (18), the pressure blocking portion (19), and the charging portion (35), which are defined by the pinch valve and are connected to the fluid tubes (9), are exposed from the controller (10). This enables the disposable portion to be set from the exterior. When used, the pressure receiving balloon (22) is set to the exposed balloon holding portion (23) and the probing portion (24), the portion of the fluid tube (9) between the bifurcating portion (30) and the waste liquid collector (37) is set to the pressure releasing portion (18), and the portion between the bifurcating portion of the fluid tube (9) and the manual pressure applying portion (17) is set to the pressure blocking portion (19).

Among the two fluid tubes, the portion of the second fluid tube (9) between the distal device (1) and the waste liquid collector (37) is set to the charging portion (35). This structure provides the same functions as that shown in FIG. 22 and enables the portion through which water flows to be disposable. Thus, hygiene problems caused by bacteria is solved.

The same effects may be obtained by using the pressure receiving piston (26) in lieu of the pressure receiving balloon (22) of the pressure fluctuation measuring portion (13) shown in FIG. 26. In this case, among the two fluid tubes (9) extending from the distal device (1), a first fluid tube (9) is connected directly to the manual pressure applying portion (17). A bifurcating portion (30) bifurcating the circuit is provided between the distal 5 device (1) and the manual pressure applying portion (17) and connected to a bag-like waste liquid collector (37). Among the two fluid tubes (9) extending from the distal device (1), a second fluid tube (9) is connected to one end of the pressure receiving piston (26). The other end of the pressure receiving piston

(26) is connected to the waste liquid collector (37). These parts define an integral disposable portion.

In the controller (10), the connecting portion of the pressure receiving piston (26), which replaces the pressure receiving portion, and the head portions of the pressure releasing portion (18), the pressure blocking portion (19), and the charging portion (35), which are defined by the pinch valve and are connected to the fluid tubes (9), are exposed from the controller (10). This enables the disposable portion to be set from the exterior. When used, the pressure receiving piston (26) is set so that its piston probing portion (47) contacts the probing portion (24), and the portion of the first fluid tube (9) between the bifurcating portion (30) and the manual pressure applying portion (17) is set to the pressure blocking portion (19). The portion of the second fluid tube (9) between the distal device (1) and the waste liquid collector (37) are set to the charging portion (35). This structure provides the same functions as that shown in FIG. 22 and enables the portion through which water flows to be disposable. Thus, hygiene problems caused by bacteria is solved.

Figure 27:
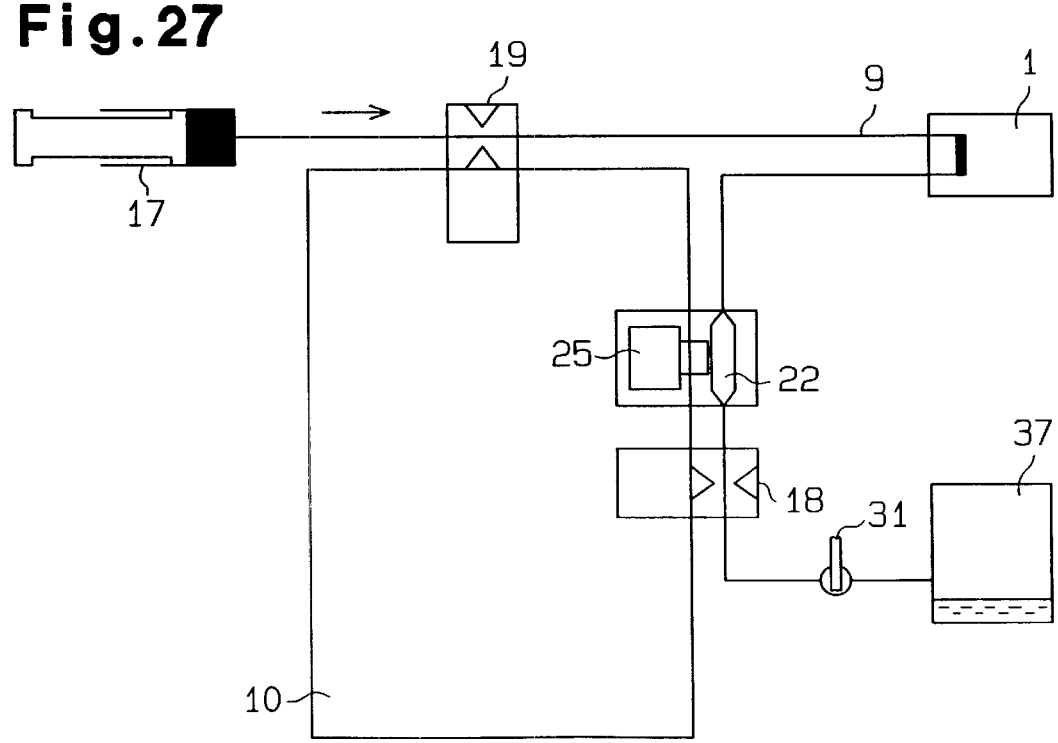
FIG. 27 is a diagram showing an embodiment using a sealed liquid as the fluid of a ligation kit and employing a pressure receiving balloon and a pinch valve.

The, embodiment of FIG. 26 was further improved to obtain the embodiment of FIG. 27 in which a liquid is sealed within the disposable portion to eliminate the need for charging a liquid before usage. The above-mentioned pressure receiving balloon (22) is used as the pressure fluctuation measuring portion (14). The above-mentioned pinch valve is used as the pressure releasing portion (18) and the pressure blocking portion (19), and the charging portion (35) is deleted. Among the two fluid tubes (9) extending from the distal device (1), a first fluid tube (9) is connected directly to the manual pressure applying portion (17). Among the two fluid tubes (9) extending from the distal device (1), a second fluid tube (9) is connected to one end of the pressure receiving balloon (22). The other end of the pressure receiving balloon (22) is connected to the waste liquid collector (37). A cock (31) is provided upstream to the waste liquid collector (37). These parts define an integral disposable portion.

Before setting the fluid tubes, liquid is charged from the manual pressure applying portion (17) through the first fluid tube (9), the distal device (1), the second fluid tube (9), and the pressure receiving balloon (22) and to the closed cock (31). In the controller (10), the connecting portion of the pressure receiving balloon (22) and the head portions of the pressure releasing portion (18), the pressure blocking portion (19), and the charging portion (35) are exposed from the controller (10). This enables the disposable portion to be set from the exterior. When used, the pressure receiving balloon (22) is set to the exposed balloon holding portion (23) and the probing portion (24), and the portion of the second fluid tube (9) between the pressure receiving balloon (22) and the cock is set to the pressure releasing portion (18). The portion of the first fluid tube (9) between the distal device (1) and the manual pressure applying portion (17) is set to the pressure blocking portion (19). By opening the cock (31) in this state, all preparations are completed and the control of separation of the ligating rings according to the present invention becomes possible without charging liquids.

The same effects may be obtained by using the pressure receiving piston (26) in lieu of the pressure receiving balloon (22) of the pressure fluctuation measuring portion (14) shown in FIG. 27. The disposable portion is charged with a liquid beforehand so that charging of the fluid is not necessary before usage. More specifically, the above-mentioned pressure receiving piston (26) is used as the pressure fluctuation measuring portion (14), the above-mentioned pinch valve is used as the pressure releasing portion (18) and the pressure blocking portion (19), and the charging portion (35) is eliminated.

A first fluid tube (9) extending from the distal device (1) is connected directly to the manual pressure applying portion (17), and a second fluid tube (9) extending from the distal device (1) is connected to one end of the pressure receiving piston (26). The other end of the pressure receiving piston (26) is connected to the waste liquid collector (37). A cock (31) is provided upstream to the waste liquid collector (37). These parts define an integral disposable portion.

Before setting the fluid tubes, liquid is charged from the manual pressure applying portion (17) through the first fluid tube (9), the distal device (1), the second fluid tube (9), and the pressure receiving balloon (22) and to the closed cock (31). In the controller (10), the connecting portion of the pressure receiving balloon (22) and the head portions of the pressure releasing portion (18), the pressure blocking portion (19), and the charging portion (35) are exposed from the controller (10). This enables the disposable portion to be set from the exterior. When used, the pressure receiving piston (26) is set so that its piston probing portion (47) contacts the sensor probing portion (24), and the portion of the second fluid tube (9) between the pressure receiving balloon (22) and the cock is set to the pressure releasing portion (18). The portion of the first fluid tube (9) between the distal device (1) and the manual pressure applying portion (17) is set to the pressure blocking portion (19). By opening the cock (31) in this state, all preparations are completed and the control of separation of the ligating rings according to the present invention becomes possible without charging liquids. Further, the same effects are obtained by using the above-mentioned pressure receiving piston (26) as the pressure fluctuation measuring portion (14).

When the liquid that is sealed in is water and if the disposable portion is sterilized with ethylene oxide gas, the water adsorbs the ethylene oxide and becomes toxic. Thus, it is preferred that silicon oil, which is not adsorbed, be used.

Figure 28:
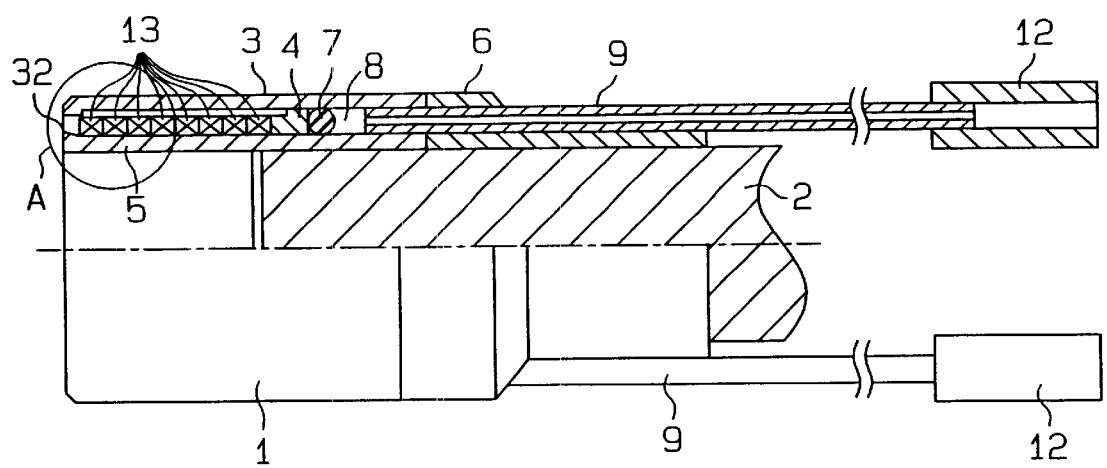
FIG. 28 is a cross-sectional view showing a state in which a distal device having a slightly projected portion in a ligation kit is attached to the endoscope.

When using the successive ligation kit, the distal device (1) is fixed to the distal end of the endoscope (2) so as to cover it as shown in FIG. 28. The requirements in this state are that the distal device (1) is securely held by the endoscope and that air does leak during suction of varices with negative pressure. The coupling tube (6) is fitted to the endoscope (2). However, if the fitting is too tight, a failure may occur in the endoscope (2). Thus, the coupling tube (6) should be made of a material having appropriate flexing and sealing properties. The preferred materials are soft plastic, rubber, and the like.

The ligating rings (13) may be formed from any material as long as the material has the elasticity required for ligating varices and causes no safety problems related to the treatment of varices. The preferred materials are natural rubber and synthetic rubber such as isoprene rubber and the like.

The inner tube (5), the outer tube (3), and the slide tube (4) are required to be thin and have high dimensional accuracy. In addition, mechanical strength for sufficiently resisting the certain level of the interior pressure in the hermetic space (8) reached during movement of the slide tube (4) is required. Thus, a hard resin is appropriate for such material. Further, it is required that the material be transparent to improve maneuverability. As long as these requirements are satisfied, any material can be used. For example, polycarbonate resin, polyvinyl chloride resin, polysulfone resin, acrylic resin, ABS (acrylonitrile-butadiene-styrene) resin, and PET (polyethylene terephthalate) resin may be used.

The seal ring (7) is required to be made of a material that keeps the hermetic space (8) in a sufficiently sealed state even when the interior pressure reaches the certain level and have a satisfactory sliding property. As such material, for example, rubber such as silicone rubber, isoprene rubber or soft plastic is preferred.

The fluid tubes (9) connected to the distal device (1) should be flexible and have a strength that resists twisting and bending when the endoscope is being manipulated. Further, the fluid tubes (9) should be capable of resisting pressure so that they are not damaged or expanded greatly when fluid is charged and the fluid circuit is pressurized. Any material satisfying these requirements may be used. Preferred materials are, for example, nylon, soft polyvinyl chloride resin, and polyurethane resin. Taking into consideration, the sensing characteristic, the length of the endoscope, and the distance between the patient and the driver (11), the length of the fluid tubes (9) should be as short as possible.

The connector (12) is the portion that connects the fluid tubes (9) to the fluid circuit in the driver (11) and divided into a distal device (1) side and a driver (11) side. The connector (12) is required to easily and detachably connect the fluid tubes and the fluid circuit of the driver Lo each other, maintain seal between the connected subject even when the interior pressure of the fluid passage reaches the certain pressure, and not fall off the connected subject. In this embodiment, although not limited to any particular structure, a tapered fitting joint provided with a locking mechanism is employed. To control the kit in the above embodiment, pressure fluctuations in the fluid circuit is measured by the pressure fluctuation measuring portion (14). The output of the pressure fluctuation measuring portion is output as a voltage proportional to the pressure. In accordance with the pressure applied by the pressure applying portion, the ligating rings (13) are separated from the distal device (1) when they pass by the front end of the inner tube (5). The pressure drops that occur during the separations are input to the differentiating circuit as a voltage drop that is proportional to the pressure value and converted to a voltage value that is proportional to the pressure fluctuation amount within a short period of time. The voltage value is compared with a threshold value in the comparator circuit. When the threshold value is exceeded, it is determined that a ligating ring (13) has been separated, and the pressure releasing portion, which is formed by an electromagnetic valve or a pinch valve, is opened instantaneously to release the interior pressure of the fluid circuit instantaneously. This stops the movement of the slide tube (4) and prevents separation of the next ligating ring (12).

In an example using the distal device (1) of FIG. 1, the pressure drop during separation of the ligating rings (13) is about 1 kgf per 10 ms. If a syringe is used manually to function as the pressure applying portion, a pressure drop that may be caused by pressure fluctuations resulting from the shaking of hands is about 1.2 kgf maximum in 10 ms and exceeds the pressure drop that occurs during ring separation. Accordingly, if the threshold value is set in correspondence with the amount of pressure drop that occurs within a short period of time during the separation of the ligating rings (13), when a pressure drop caused by pressure fluctuations resulting from the shaking of hands reaches the maximum level, the output of the differentiating circuit exceeds the threshold value. Thus, it is erroneously determined that a ligating ring (13) has been separated. This may cause a failure and stop the movement of the ligating ring (13) when the ligating ring (12) has not yet been separated.

Figure 29:
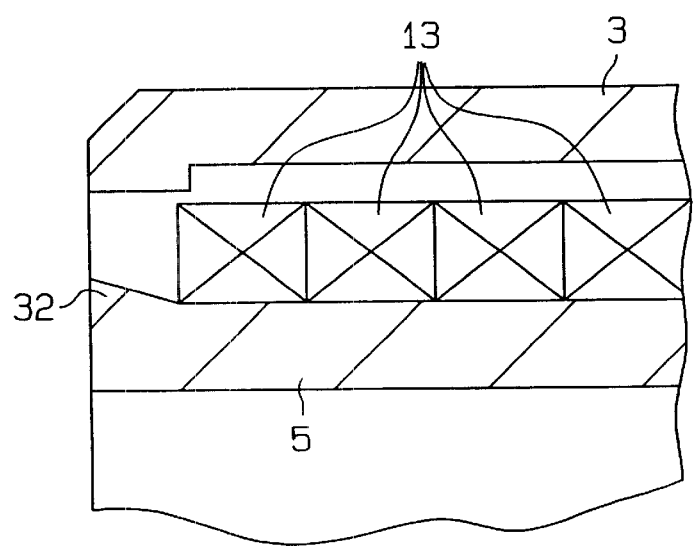
FIG. 29 is an enlarged cross-sectional view of portion A in FIG. 28 showing the slightly projected portion in detail.

To prevent such failure, it is desirable that the structure of the distal device (1) shown in FIG. 28 be employed. More specifically, the ring-like slide tube (4) is accommodated in the cylindrical outer tube (3), and the cylindrical inner tube (5) is inserted into the inner cavity of the slide tube (4). As shown in FIG. 29, a ring-like slightly projected portion (32) is formed on the peripheral surface at the distal end of the inner tube (5). The slide tube (4) is movable along the center axis of the distal device (1). The movement of the slide tube (4) toward the distal end is restricted by the interference between the distal end of the slide tube (4) and the slightly projected portion (32).

Regardless of the shape and size of the slightly projected portion (32), in this embodiment, the slightly projected portion (32) is formed so that its cross-section is tapered and the diameter at the distal end of the slightly projected portion (32) is maximum, as illustrated in FIG. 29, which shows in detail the cross-section of portion A of FIG. 28. The load for pushing out the ligating rings (13) with the slide tube (4) increases as the maximum height of the tapered portion increases and the angle of the tapered portion increases. Accordingly, the height and angle is required to be set so that the load produced by the slide tube (4) enables the ligating rings (13) to pass by the slightly projected portion and through the gap between the outer tube (3) and the slightly projected portion (32) when a maximum number, or eight, of the ligating rings (13) are held b)y the distal device (1).

Figure 30:
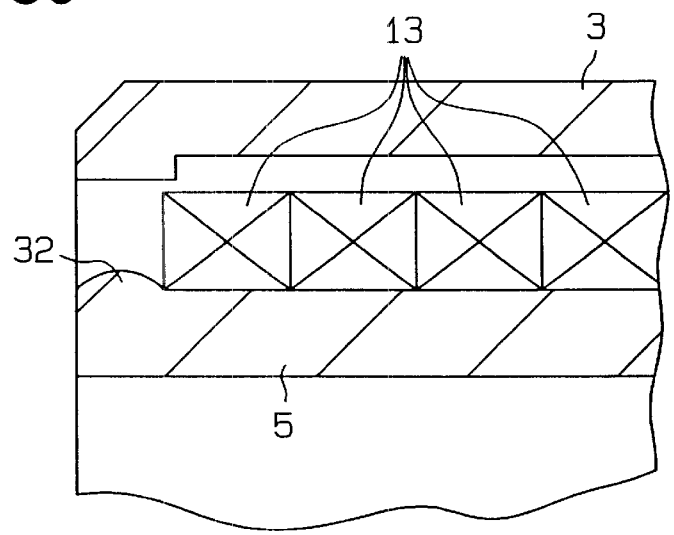
FIG. 30 is a cross-sectional view showing a further embodiment of a slightly projected portion in correspondence with FIG. 29.

In this embodiment, the maximum height of the slightly projected portion is 0.1 to 1.0 mm, and especially preferred that the height be 0.4 to 0.6 mm. The angle is 5 to 30°, and especially preferred that the angle be 10 to 20°. The eight ligating rings (12) are separated with a load of 5 to 20 kgf produced by the slide tube (4) of the distal device (1). If the thickness of the ligating rings (13) is 1.0 to 2 mm, the gap between the outer tube (3) and the maximum diameter part of the slightly projected portion (32) is set to be about 1.2 times greater at 1.2 to 2.4 mm. If the above requirements are satisfied, the slightly projected portion (32) may be formed to have a round cross-section as shown in FIG. 30.

When the slightly projected portion (32) is provided, the movement load increases in comparison to the distal device (1) of FIG. 1 in which the slightly projected portion (32) is not provided at the distal end of the inner tube (5). Thus, the pressure of the fluid circuit immediately before separation of the ligating rings (13) when the ligating rings pass by the slightly projected portion (32) increases. As a result, the amount of pressure drop that occurs during the small period of time after the ligating rings are separated increases.

The pressure drop of the distal device (1) of FIG. 1, which does not have the slightly projected portion (32), is 1 kgf per 10 ms. In comparison, the pressure drop in this embodiment, in which the slightly projected portion (32) is added to the distal device of FIG. 1, is 2 to 5 kgf per 10 ms. The pressure drop caused by the shaking of hands is about 1.2 kgf per 10 ms. Thus, by setting the threshold value of the comparator circuit at 1.2 kgf or more per 10 ms and within a range of 2–5 kgf, failures caused by the shaking of hands is prevented. This results in the controller responding only when the ligating rings (13) are separated.

The distal device (1) of this embodiment is attached to the distal end of the endoscope. Since the ligating rings (13), which are not light permeable, covers the front portion of the distal device (1), the view of the endoscope is blocked. To improve the view, the relative distance between an endoscope lens, which is located at the distal end of the endoscope, and the frontmost portion of the ligating rings

(13) must be shortened. However, during suction of a lesion, the volume of the space between the inner surface of the inner tube (5) and the distal surface of the endoscope must be sufficient, and the distance between the distal surface of the endoscope and the distal device (1) is required to be 8 to 12 mm. If the ligating rings (13) are normally located at the distal portion like in the distal device (1) shown in FIG. 1 and FIG. 28, it is impossible to obtain the desirable view while facilitating suction.

Figure 31:
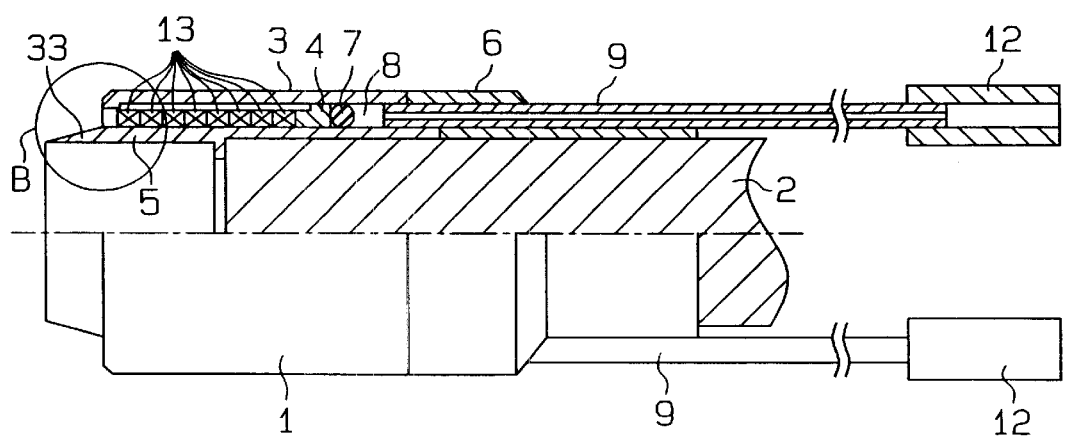
FIG. 31 is a cross-sectional view showing a state in which a distal device having a hood in a ligation kit is attached to the endoscope.
Figure 32:
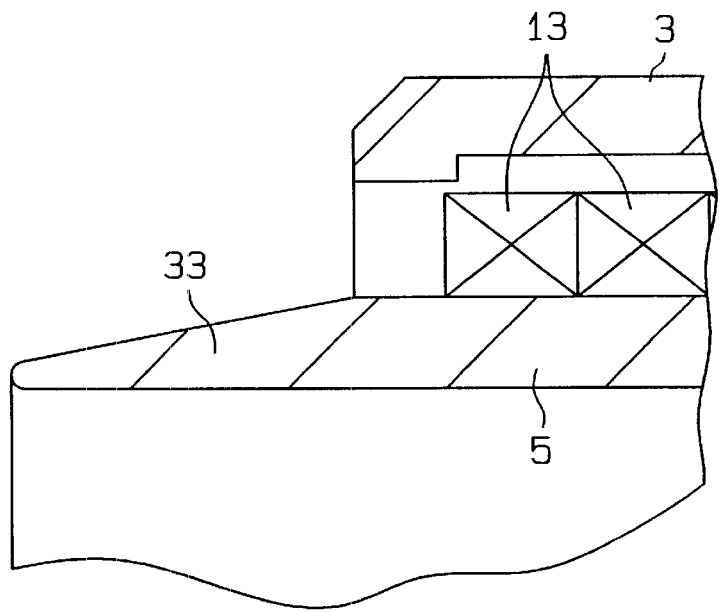
FIG. 32 is an enlarged cross-sectional view of portion B in FIG. 31 showing the hood in detail.

Accordingly, in an improved embodiment illustrated in FIG. 31 and FIG. 32, which shows the cross-section of portion B of FIG. 31 in detail, a tapered hood (33) is arranged at the distal portion of the inner tube (5). As described above, the relative distance between the endoscope lens located at the distal end of the endoscope and the frontmost portion of the ligating rings (13) is shortened to improve the view. The distance between the distal surface of the endoscope and the distal surface of the distal device (1) is compensated for by the length of the hood (33). The reason for tapering the hood is to prevent the application of external forces to the ligating rings (13) when the ligating rings passes by a separation point (34), which is located at the basal end of the hood (33), and to facilitate separation using the ligating force of the rings. In other words, in a normal state when separation is not being performed, the ligating rings (13) are located at the rear of the separation point. Thus, in comparison with the distal devices (1) of FIG. 1 and FIG. 28, the relative distance between the endoscope lens located at the distal end of the endoscope and the frontmost portion of the ligating rings (13) is shortened and the view is improved.

It is required that the hood (33) have a taper angle that enables separation using the ligating force of the ligating rings (13) when the ligating rings (13) passes by the separation point (34). Further, a certain distance is required between the distal surface of the endoscope and the distal surface of the distal device (1) to guarantee suction. Thus, in this embodiment, the tapered angle is 13° to 20° and ideally 14° to 16°. The length of the tapered hood is 2 to 7 mm, and ideally 3 to 5 mm. Like the inner tube (5), the hood (33) is required to be made of a transparent material. Although the material is not limited, materials such as polycarbonate resin, polyvinyl chloride resin, polysulfone resin, acrylic resin, ABS resin, and PET resin may be used.

Figure 33:
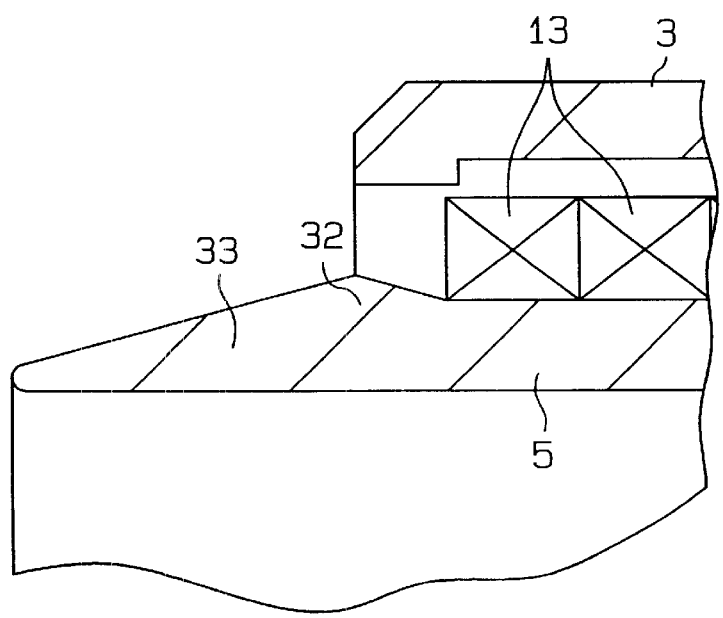
FIG. 33 is a cross-sectional view showing a further embodiment provided with a hood and a small projection portion and corresponding to FIG. 32.
Figure 34:
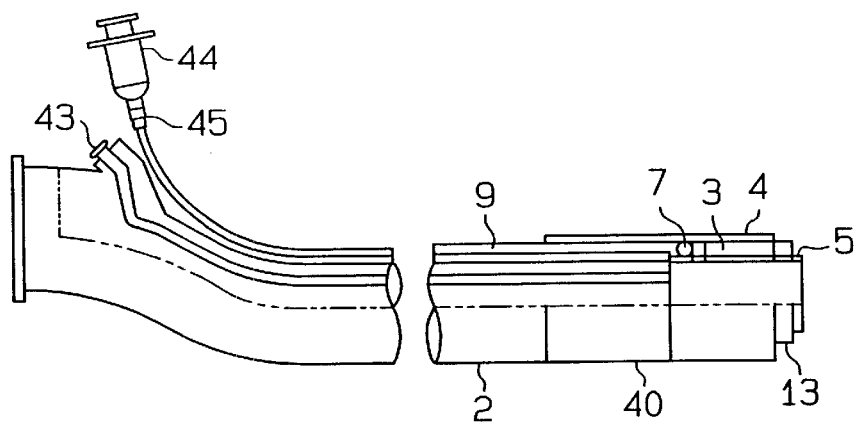
FIG. 34 is a front view showing a prior art endoscope ligation instrument.
Figure 35:
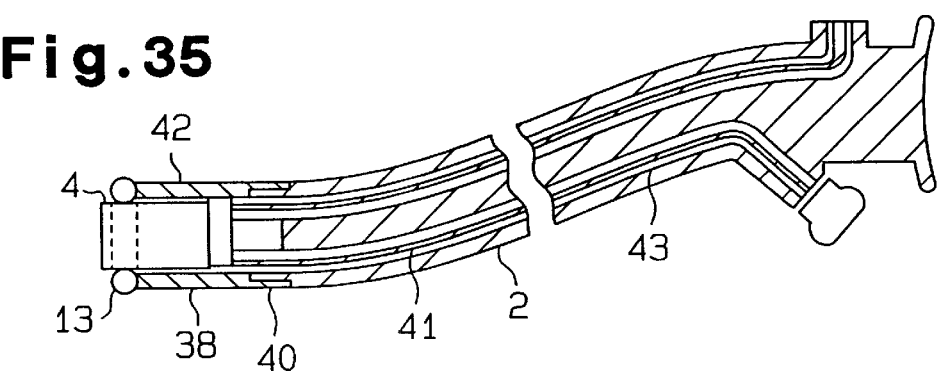
FIG. 35 is a cross-sectional view showing a prior art endoscope ligation instrument.
Figure 36:
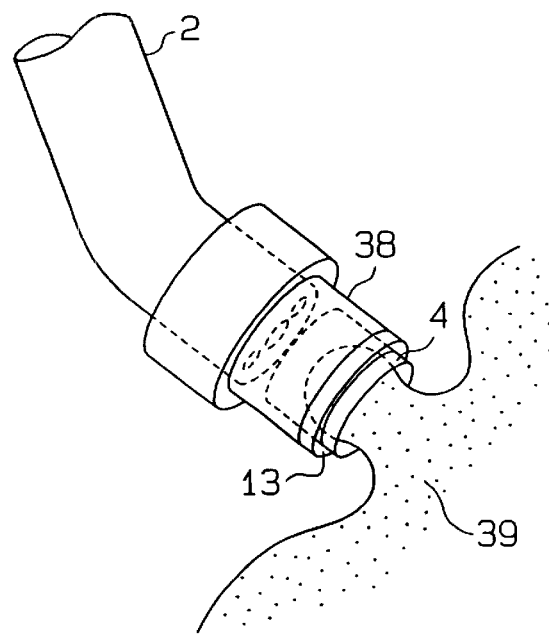
FIG. 36 is a perspective view showing how an endoscope ligation instrument is used.

Further, to obtain the failure preventing effect of the slightly projected portion (32) and the effect of the tapered hood (33) at the same time, these two may be combined as shown in FIG. 33.

The successive ligation kit according to the present invention obtains superior effects in which the separation of a certain number of ligating rings is guaranteed, a certain ligating force that corresponds to a lesion is obtained, accidental non-separation of the ligating rings and accidental separation of the ligating rings do not occur, and treatment in accordance with the conditions of various types of lesions is possible.

What is claimed is:

1. A ligation apparatus comprising:
   a device adapted to be attached to the distal end of an endoscope, wherein the device supports a plurality of ligating rings and ligates a lesion when an operator separates at least one ring and attaches the ring to the lesion;
   a pump for delivering fluid to the device, wherein each ring is separated by fluid delivered to the device by the pump;
   a fluid circuit located between the device and the pump;
   a controller connected to the fluid circuit to control the movement of the ligating rings, wherein the controller senses pressure variation in the fluid when one of the rings is separated, and wherein the movement of the ligating rings is controlled by sensing the pressure variation.

2. The ligation apparatus according to claim 1, wherein the controller determines the number of rings that have been separated based on the pressure variation.

3. The ligation apparatus according to claim 1, wherein the pump is a manual pump.

4. The ligation apparatus according to claim 1 further comprising a valve for selectively opening and closing the fluid circuit in accordance with an electric control signal, wherein the pressure in the fluid circuit is reduced by the valve to stop movement of the rings on the device.

5. The ligation apparatus according to claim 4, wherein the valve is located between the pump and the fluid circuit.

6. The ligation apparatus according to claim 4, wherein the valve is electromagnetic.

7. The ligation apparatus according to claim 1, wherein the fluid is a liquid.

8. The ligation apparatus according to claim 1, wherein the device includes a support for guiding movement of the rings, wherein the rings surround and slide on the support.

9. The ligation apparatus according to claim 8, wherein the support includes a projection for creating resistance to the movement of the rings.

10. The ligation apparatus according to claim 9, wherein the projection is annular.

11. The ligation apparatus according to claim 8, wherein the device has a tapered hood.

12. The ligation apparatus according to claim 1, wherein the apparatus includes a pressure detector for sensing a pressure change in the fluid circuit.

13. The ligation apparatus according to claim 12, wherein the pressure detector includes a balloon, and wherein pressure variations of the fluid are detected by measuring the pressure inside the balloon.

14. The ligation apparatus according to claim 13, wherein the balloon is connected to the fluid circuit by a funnel-like connector.

15. The ligation apparatus according to claim 12, wherein the pressure detector includes a hermetic chamber connected to the fluid chamber, and a piston is located in the hermetic chamber, wherein pressure variations of the fluid are detected by measuring movement of the piston.

16. The ligation apparatus according to claim 1, wherein the controller including a differentiating circuit and a comparator circuit for converting sensed pressure variations into electrical signals.

17. The ligation apparatus according to claim 16, wherein the controller processes the sensed pressure variations within a predetermined time, wherein the predetermined time is based on the time between successive ring separations.

18. A ligation apparatus comprising:

a device adapted to be attached to the distal end of an endoscope, wherein the device supports a plurality of ligating rings and ligates a lesion when an operator separates at least one ring and attaches the ring to the lesion;

a pump means for delivering fluid to the device, wherein each ring is separated by fluid delivered to the device by the pump means;

a fluid circuit located between the device and the pump means;

a controller means connected to the fluid circuit to control the movement of the ligating rings, wherein the controller senses pressure variation in the fluid when one of the rings is separated, and wherein the movement of the ligating rings is controlled by sensing the pressure variation.

19. The ligation apparatus according to claim 18, wherein the controller means determines the number of rings that have been separated based on the pressure variation.

20. The ligation apparatus according to claim 18 further comprising a valve means for selectively opening and closing the fluid circuit in accordance with an electric control signal, wherein the pressure in the fluid circuit is reduced by the valve means to stop movement of the rings on the device.

* * * * *